US010335061B2

(12) United States Patent
Azaria et al.

(10) Patent No.: US 10,335,061 B2
(45) Date of Patent: Jul. 2, 2019

(54) METHODS AND APPARATUS FOR DETECTING HAND-TO-MOUTH BEHAVIOR

(71) Applicant: Massachusetts Institute of Technology, Cambridge, MA (US)

(72) Inventors: Asaph Azaria, New York, NY (US); Brian Mayton, Somerville, MA (US); Joseph Paradiso, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 427 days.

(21) Appl. No.: 15/331,840

(22) Filed: Oct. 22, 2016

(65) Prior Publication Data

US 2017/0127979 A1 May 11, 2017

Related U.S. Application Data

(60) Provisional application No. 62/252,476, filed on Nov. 7, 2015.

(51) Int. Cl.
*A61B 5/053* (2006.01)
*A61B 5/11* (2006.01)
*A61B 5/00* (2006.01)

(52) U.S. Cl.
CPC ............ *A61B 5/1123* (2013.01); *A61B 5/053* (2013.01); *A61B 5/1114* (2013.01); *A61B 5/1128* (2013.01); *A61B 5/6824* (2013.01); *A61B 5/7267* (2013.01); *A61B 2562/0209* (2013.01); *A61B 2562/0219* (2013.01); *A61B 2562/0223* (2013.01); *A61B 2562/043* (2013.01); *A61B 2562/06* (2013.01)

(58) Field of Classification Search
None
See application file for complete search history.

(56) References Cited

U.S. PATENT DOCUMENTS 4,557,275 A  *  12/1985  Dempsey, Jr. ....... A61B 5/1124
                                                  340/573.1
4,965,553 A     10/1990  DelBiondo, II et al.
(Continued)

OTHER PUBLICATIONS

Ayllon, D., et al., Cole equation and parameter estimation from electrical bioimpedance spectroscopy measurements—a comparative study; published in 2009 Annual International Conference of the IEEE Engineering in Medicine and Biology Society, pp. 3779-3782. IEEE, 2009.

(Continued)

*Primary Examiner* — Peter J Macchiarolo
*Assistant Examiner* — Jermaine L Jenkins
(74) *Attorney, Agent, or Firm* — Stephen R. Otis

(57) ABSTRACT

A sensor system detects hand-to-mouth behavior. The system includes an electrical bio-impedance spectrometer and an inertial measurement unit. The sensor system may be worn on the forearm. The sensor system recognizes hand-to-mouth behavior in real-time, facilitating monitoring and immediate interventions An electrode positioning strategy optimizes the device's sensitivity and accuracy. Machine learning algorithms are leveraged to infer the hand-to-mouth detection. A prototype of the sensor system achieves 92% detection accuracy for recurrent usage by a single user and 90% accuracy for users that have not been previously encountered.

18 Claims, 8 Drawing Sheets

(56) References Cited

U.S. PATENT DOCUMENTS

| | | | |
|---|---|---|---|
| 6,093,158 A | 7/2000 | Morris | |
| 6,762,687 B2 | 7/2004 | Perlman | |
| 7,050,847 B2* | 5/2006 | Ollmar | A61B 5/0531 600/365 |
| 7,126,483 B2* | 10/2006 | Zarouri | G08B 21/18 340/573.1 |
| 7,476,102 B2* | 1/2009 | Maples | A61F 5/013 434/247 |
| 9,675,294 B2* | 6/2017 | Levin | A61M 1/1611 |
| 2007/0100666 A1 | 5/2007 | Stivoric et al. | |
| 2017/0367614 A1* | 12/2017 | Zuckerman-Stark | A61B 5/6831 |

OTHER PUBLICATIONS

Ayllon, D., Methods for Cole Parameter Estimation from Bioimpedance Spectroscopy Measurements: A Comparitive Study; published as Master Degree Thesis, University of Boras, School of Engineering, 2009.

Blomqvist, K., et al., An open-source hardware for electrical bioimpedance measurement; published in IEEE 2012 13th Biennial Baltic Electronics Conference, pp. 199-202, Oct. 2012.

Cornish, B., et al., Improved prediction of extracellular and total body water using impedance loci generated by multiple frequency bioelectrical impedance analysis; published in Physics in Medicine and Biology, 38(3), pp. 337-346 (1993).

Madgwick, S., et al., Estimation of IMU and MARG orientation using a gradient descent algorithm; published in 2011 IEEE International Conference on Rehabilitation Robotics, pp. 1-7 (Jun. 2011).

Sato, M., et al., Touche: enhancing touch interaction on humans, screens, liquids, and everyday objects; published in Proceedings of the SIGCHI Conference on Human Factors in Computing Systems, pp. 483-492, ACM (May 2012).

Sato, M., et al., Zensei: Augmenting Objects with Effortless User Recognition Capabilities through Bioimpedance Sensing; published in Adjunct Proceedings of the 28th Annual ACM Symposium on User Interface Software & Technology, pp. 41-42, ACM, 2015.

Seoane, F., et al., An analog front-end enables electrical impedance spectroscopy system on-chip for biomedical applications; published in Physiological measurement 29, No. 6 (2008), S267.

Seoane, F., et al., Cole parameter estimation from electrical bioconductance spectroscopy measurements, published in 2010 Annual International Conference of the IEEE Engineering in Medicine and Biology, pp. 3495-3498. IEEE, 2010.

* cited by examiner

METHODS AND APPARATUS FOR DETECTING HAND-TO-MOUTH BEHAVIOR

RELATED APPLICATIONS

This application claims the benefit of U.S. Provisional Patent Application No. 62/252,476, filed Nov. 7, 2015, the entire disclosure of which is herein incorporated by reference.

FIELD OF TECHNOLOGY

The present invention relates generally to detecting hand-to-mouth behavior.

COMPUTER PROGRAM LISTING

Attached are seventeen computer program files, each of which were created as a .txt file on Oct. 7, 2016: (1) RT_receiver.txt with a size of about 14 KB; (2) Adaboost_classifier.txt with a size of about 3 KB; (3) AHRS.txt with a size of about 9 KB; (4) AHRS_tester.txt with a size of about 5 KB; (5) Classification.txt with a size of about 5 KB; (6) ColeColeParameterEstimation.txt with a size of about 7 KB; (7) DatasetsManager.txt with a size of about 12 KB; (8) EBI_offline_viewer.txt with a size of about 8 KB; (9) Electrode_configuration_analysis.txt with a size of about 6 KB; (10) GMM_classifier.txt with a size of about 2 KB; (11) KNN_classifier.txt with a size of about 3 KB; (12) LogisticRegression.txt with a size of about 3 KB; (13) MultipleAlgClassifier.txt with a size of about 4 KB; (14) RandomForest_classifier.txt with a size of about 5 KB; (15) RT_EBIScaler.txt with a size of about 5 KB; (16) RT_IMU_scaler.txt with a size of about 6 KB; and (17) SVM_classifier.txt with a size of about 6 KB. These seventeen computer program files comprise software employed in a prototype implementation of this invention. These seventeen computer program files are each incorporated by reference herein.

BACKGROUND

Hand-to-mouth compulsive habits, such as thumb sucking and nail biting, are surprisingly common. Studies found that 28-33% of children, 44% of adolescents, and 19-29% of young adults engage in nail biting alone. These compulsive habits expose those who exhibit them to multiple health risks, including risks of expedited transmission of diseases, dental malocclusion and even abnormal facial development.

Electrical bio-impedance (EBI) describes the electrical properties biological materials exhibit as current flows through them. EBI is commonly measured by injecting a small sinusoidal alternating current (AC) into the tissue under study. The injected current induces an electrical field within the tissue and results in a measurable voltage drop across it. The AC version of Ohm's Law (Equation 1) relates the tissue's electrical bio-impedance Z to the ratio between the voltage V (i.e., the voltage drop across the tissue) and the injected current I.

$$Z = \frac{V}{I} \quad \text{Eq. 1}$$

Z is a complex quantity, since biomaterials not only oppose current flow, but also store electrical charge and phase-shift the voltage with respect to the current in the time-domain.

When current flows through a tissue, it passes through extracellular and intracellular fluids. These fluids are highly conductive as they contain salt ions that can easily be displaced by a potential difference. Conversely, the cells' lipid membranes are insulators. They act like capacitive plates, which prevent electrical charges from flowing through. Accordingly, the tissue's impedance reflects its chemical composition, membrane structures, and fluids distribution. For similar reasons, the specific cell types (blood, adipose, muscle, bone, etc.), the anatomic configuration (i.e., bone or muscle orientation and quantity), and the state of the cells (normal or osteoporotic bone, oedematous vs. normally hydrated tissue, etc.) affect measured impedance quantities.

Most tissues display dispersive characteristics, i.e. their impedance varies with the frequency of the applied current. A typical dispersion curve may be plotted as a Cole-Cole plot which superimposes impedance measurements from a range of frequencies on the complex plane. At low frequencies, the cells' membranes block the current. Thus, the impedance corresponds only to the extracellular resistance. As frequency increases, more current passes through the intracellular capacitive path, and the phase angle accumulates. At high frequencies, the intracellular capacitance becomes negligible. The impedance is once again purely resistive, dominated by the intracellular and extracellular fluid resistances connected in parallel. The frequency at which the tissue's reactance reaches a peak is known as the center frequency ($f_c$).

A simple electrical circuit that may be used to model EBI response is $(R_i+C_m)) \| R_e$, that is, $R_e$ in parallel with the series combination of $R_i$ and $C_m$. In this model, $R_i$ is intracellular resistance; $R_e$ is extracellular resistance, and $C_m$ is cell membrane capacitance. This model results in a perfect semicircle in a Cole-Cole plot, with the center of the circle on the resistance axis.

In real tissue, however, the cells' membrane is an imperfect capacitor. Moreover, the large variation in cell type, structure, and size causes a distribution of the cells' capacitive time constants. Cole and Cole showed that when capacitive time constant distribution is added to the above circuit model, the impedance is related to the frequency by:

$$Z = R_\infty + \frac{R_0}{1+(j\omega\tau)^{1-\alpha}} \quad \text{Eq. 2}$$

where $$R_0 = R_e \quad \text{Eq. 3}$$

$$R_\infty = R_i \| R_e \quad \text{Eq. 4}$$

$$\tau = (R_e + R_i) C_m \quad \text{Eq. 5}$$

In Equations 2-5 above, $\omega$ is angular frequency of electrical current in radians per second, Z is complex impedance (in ohms), $R_0$ is resistance (in ohms) at zero frequency, $R_\infty$ is resistance (in ohms) at infinite frequency, $\tau$ is a time constant (in seconds) that is the inverse of the characteristic frequency $\omega_c$, and $\alpha$ is a dimensionless exponent that is proportional to depression angle, as discussed below.

This model preserves the circular shape in a Cole-Cole plot, but depresses the circle's center below the resistance axis. α has a value between 0 and 1, and is proportional to the angle to the depressed center.

Two types of electrode systems are commonly used to obtain EBI measurements. A two-electrode system uses the same pair of electrodes to inject current (IC) and pick up (PU) the tissue's response.

A four-electrode system uses different pairs for excitement and pick up. A pair of IC (inject current) electrodes drive current into tissue and a pair of PU (pick up) electrodes measure voltage response of the tissue. The type of electrodes in use (needle or skin surface, gel or dry, etc.), and their configuration around the tissue affect the sensed impedance almost as much as the electrical properties of the tissue.

The electrode type determines how the electrical conductor in the measurement leads interfaces with the ionic conductor in the biological tissue. As current flows, substance concentration may change near the electrodes' interface, adding bias impedance called electrode polarization. The skin-electrode contact introduces an additional resistive bias. The four-electrode system is a robust setup that reduces the influence of these factors. When voltage pick up is implemented with high-impedance differential amplifiers, such artifacts can be neglected.

The electrode configuration sets boundary values on the electrical fields that develop inside the tissue. Thus, it governs the fields' propagation and in effect, the relative contribution of internal tissue regions to the measured mutual impedance. For a four-electrode system, the measured impedance Z resulting from the variable conductivity σ within a volume conductor can be evaluated by:

$$Z = \int_V \frac{1}{\sigma} S dv \qquad \text{Eq. 6}$$

Sensitivity S is a scalar field, determining the contribution of a local conductivity change (Δσ) to the overall potential. It may be calculated from the dot product of two current density fields:

$$S = \vec{J}_{IC} \cdot \vec{J}_{PU} \qquad \text{Eq. 7}$$

$\vec{J}_{IC}$ represents the current density field generated by a unit current applied through the IC electrodes. $\vec{J}_{PU}$ is the reciprocal current density field that would have been generated had the same current been injected through the PU electrodes.

Depending on the angle of the two fields, there may be regions where the sensitivity is zero, positive, or negative. Hence, the tissue regions, in which impedance changes are measured, may effectively be manipulated by the electrode configuration. The measured mutual impedance may be indifferent to interchanges between the IC and PU electrodes.

SUMMARY

In illustrative implementations of this invention, a sensor system detects hand-to-mouth behavior. The system includes an electrical bio-impedance (EBI) spectrometer and an inertial measurement unit (IMU). The sensor system may be worn on the forearm. The sensor system recognizes hand-to-mouth behavior in real-time, facilitating monitoring and immediate interventions An electrode positioning strategy optimizes the device's sensitivity and accuracy. Machine learning algorithms are employed to detect hand-to-mouth behavior. A prototype of the sensor system achieves 92% detection accuracy for recurrent usage by a single user and 90% accuracy for users that have not been previously encountered.

In illustrative implementations, the IMU tracks the forearm's orientation. The EBI spectrometer electrically excites the forearm and measures changes in impedance of the forearm. One or more computers analyze the IMU and EBI sensor measurements to infer hand-to-mouth behavior in real-time. The sensor system performs automated detection of hand-to-mouth behavior.

In illustrative implementations, four electrodes of the EBI spectrometer are electrically connected to the forearm. Two are IC (inject current) electrodes for driving an alternating electrical current through the forearm. The other two are PU (pick up) electrodes for measuring a voltage drop between the two PU electrodes. The voltage drop occurs due to impedance in tissue, including in the forearm. The EBI spectrometer drives the AC current in frequency sweeps.

In illustrative implementations, the four electrodes are positioned on the skin of the forearm in a crossed configuration, instead of in a conventional, parallel configuration. Experimental data from a test of a prototype of this invention indicates that the crossed electrode configuration yields results that are more accurate and sensitive to change in EBI, than results obtained with a conventional, parallel configuration of electrodes. Without being limited by theory, the crossed configuration of electrodes on the forearm appears to make the EBI measurements more sensitive to hand-to-mouth behavior, where the fingers being inserted into the mouth occurs at a distance from the four forearm electrodes.

In illustrative implementations, the four electrodes may be positioned on the forearm in either a (6,5) configuration or a (10,1) configuration, as those terms are used herein. For purposes of describing these two configurations: (a) the forearm is treated as being indexed along its proximal-distal axis into ten positions, ranging from position ten (most proximal, adjacent to elbow) to position one (most distal, closest to wrist). Thus, positions five and six are located approximately halfway along the proximal-distal axis of the forearm.

The description of the present invention in the Summary and Abstract sections hereof is just a summary. It is intended only to give a general introduction to some illustrative implementations of this invention. It does not describe all of the details and variations of this invention. Likewise, the description of this invention in the Field of Technology section is not limiting; instead it identifies, in a general, non-exclusive manner, a technology to which exemplary implementations of this invention generally relate. Likewise, the Title of this document does not limit the invention in any way; instead the Title is merely a general, non-exclusive way of referring to this invention. This invention may be implemented in many other ways.

BRIEF DESCRIPTION OF THE DRAWINGS

FIGS. 3A and 3B show views of the anterior side and posterior side, respectively, of the same forearm of the subject. In FIG. 3A, a first row of ten electrodes are attached to the skin of the anterior side of the forearm. In FIG. 3B, a second row of ten electrodes are attached to the skin of the posterior side of the forearm.

The above Figures show some illustrative implementations of this invention, or provide information that relates to those implementations. However, this invention may be implemented in many other ways.

DETAILED DESCRIPTION

Hardware

In illustrative implementations of this invention, a sensor system detects hand-to-mouth behavior. The sensor system includes an inertial measurement unit (IMU) and an EBI spectrometer. The EBI spectrometer detects distinct impedance spectra that result from different hand positions, including inserting a hand into a mouth. The sensor system employs machine-learning techniques to distinguish between different hand positions, including placing a hand inside a mouth.

Figure 1:
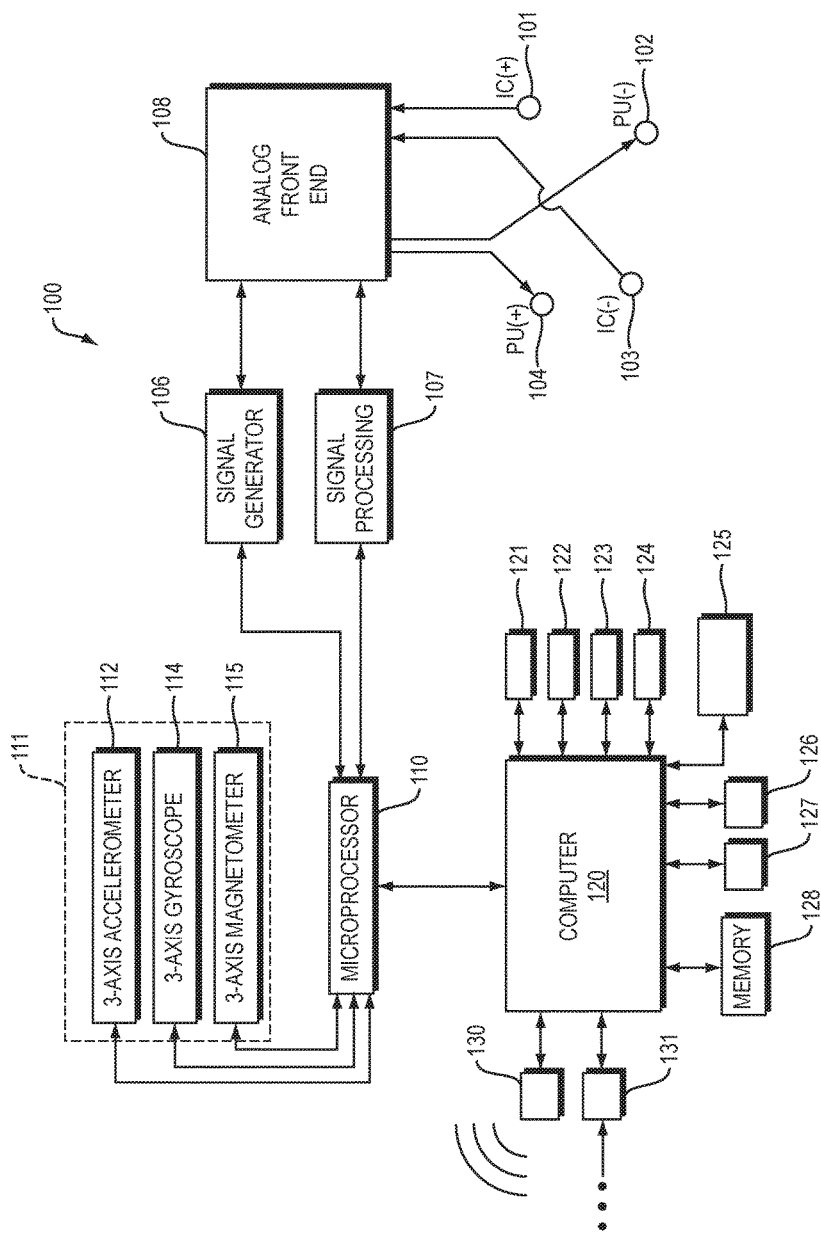
FIG. 1 is a diagram of a system for detecting hand-to-mouth behavior.

FIG. 1 is a diagram of a sensor system 100 for detecting hand-to-mouth behavior, in an illustrative implementation of this invention. The sensor system 100 includes an IMU 111 and an EBI spectrometer. The IMU 111 comprises a 3-axis accelerometer 112, 3-axis gyroscope 114, and 3-axis magnetometer 115. The IMU 111 is attached to a strap or band, and is worn around the wrist or lower forearm of a user. The IMU 111 detects changes in orientation or position of the forearm, and thus of the hand. The EBI spectrometer includes a signal generator 106, analog front end 108, IC (inject current) electrodes 101, 103, PU (pick up) electrodes 102, 104 and signal processing unit 107. The signal generator 106 generates an AC (alternating current) electrical voltage signal. The analog front end 108 converts the AC voltage signal into an AC current signal. The IC electrodes 101, 103 apply the AC current signal to the tissue. The PU electrodes 102,104 pick up the voltage response of the tissue. The analog front end 108 converts the analog voltage signal (that is received by the PU electrodes from the tissue) into an analog electrical current signal. The signal processor 107 converts the analog signal into a digital signal. The signal processor 107 compares the received current signal to the sent voltage signal and calculates the complex impedance (resistance and reactance) for the particular frequency that was induced. The signal processor then sends the two values (resistance and reactance) for the particular frequency to the microprocessor, which can then instruct that impedance at a different frequency be measured.

In the example shown in FIG. 1, a microprocessor 110 controls the signal generator 106. Microprocessor 110 also receives sensor data from the IMU 111 and from the EBI spectrometer. In some cases, microprocessor 110 extracts features from the sensor data (such as quaternions from the IMU sensor data, and Cole-Cole model parameters from the EBI data). The microprocessor sends sensor data, or features extracted from sensor data, to a computer 120. The computer 120 processes data from the microprocessor to detect hand-to-mouth behavior. The computer 120 may control one or more input/output (I/O) devices that output information in a form that is perceptible to a human, including a touch screen 125, a speaker 126, or a computer monitor screen 127. The computer 120 may control and interface with one or more I/O devices that receive input from a human user, including a keyboard 121, mouse 122, microphone 123, camera 124, and touch screen 125. The computer 120 may interface with (i) a wireless communication module 130, (ii) a network communication module 131 for communication over a wire or fiber-optic link, or (iii) both. The computer 120 may store data in and retrieve data from a memory device 128.

In some implementations, the sensor system transforms matter by altering a material property of matter that is external to the sensor system. Specifically, in some implementations, the sensor system changes impedance of tissue, in that: (a) the system injects AC current into tissue that is external to the sensor system, and performs frequency sweeps in which the frequency of the current changes over time; and (b) the changes in frequency cause the impedance of the tissue to change.

Prototype, Generally

The following discussion describes a prototype implementation of this invention, including (a) hardware, software and operation of the prototype, and (b) results regarding tests of the prototype's sensitivity and accuracy. This prototype is a non-limiting example of this invention. This invention may be implemented in many ways, other than this prototype.

Prototype Hardware

Figure 2:
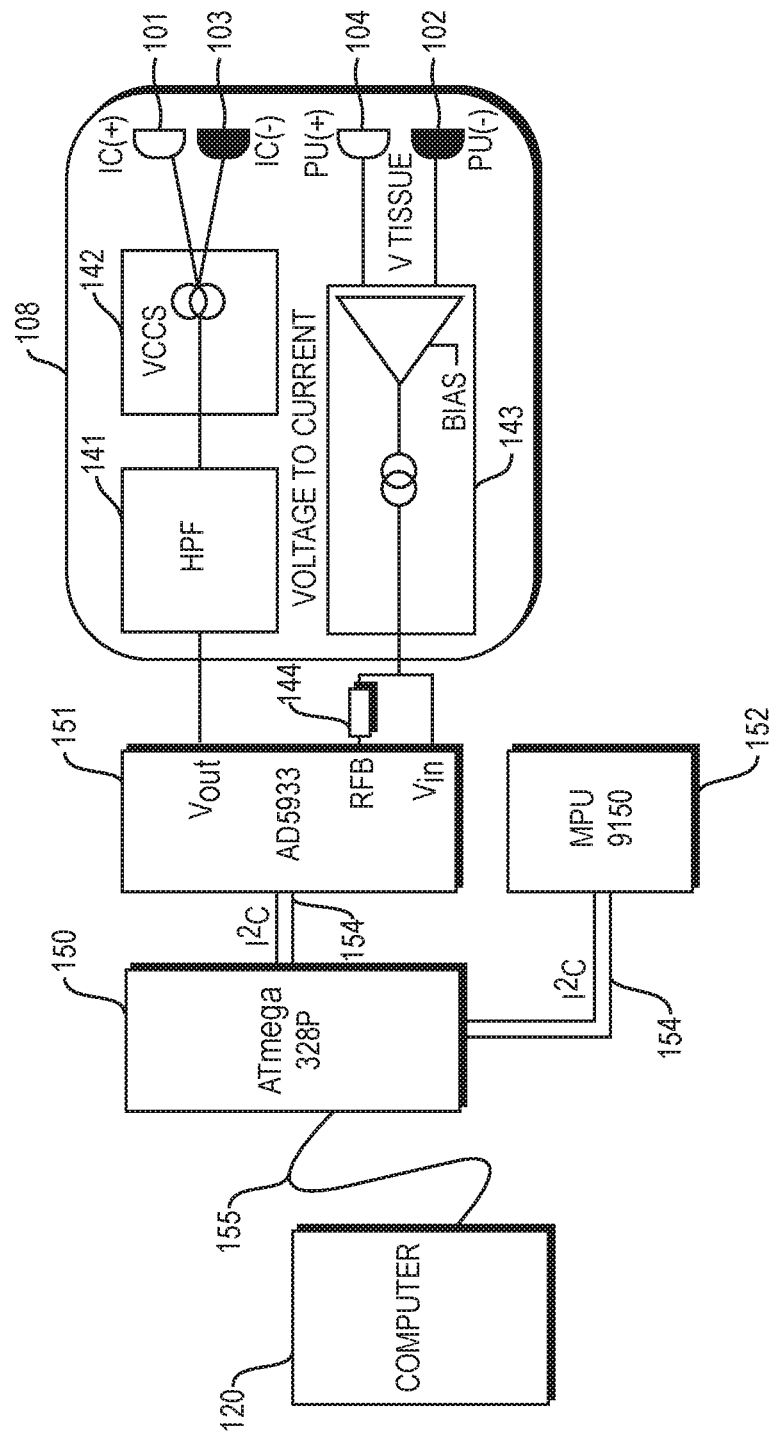
FIG. 2 is a diagram of hardware for a prototype.

FIG. 2 is a diagram of hardware for this prototype.

In this prototype (which is shown in FIG. 2), the EBI spectrometer is implemented on a printed circuit board and includes an Analog Devices™ AD5933 on-chip network analyzer. The AD5933 analyzer 151 includes a frequency generator for outputting a sinusoidal excitation voltage. The response signal is picked up by the AD5933 network analyzer 151 and processed by on-chip Discrete Fourier Transform. Real and imaginary 16-bit data words, proportional to the measured impedance, are returned for each output frequency. A frequency range between 1 to 100 kHz is supported, with a 0.1 Hz resolution.

In this prototype, the AD5933 network analyzer 151 interfaces with an analog front end 108, in a manner similar to that described in F. Seoane et al., "*An analog front-end enables electrical impedance spectroscopy system on-chip for biomedical applications*", Physiological Measurement, Volume 29, pages S267-S278, Jun. 11, 2008. The analog front-end 108 converts the AD5933 from a 2-electrode to a four-electrode measurement system. Hence, the analog front-end 108 cancels impedance contributions from electrode polarization and skin-electrode coupling. The analog front end 108 includes a voltage controlled current source (VCCS) 142 that modifies the AD5933 excitation from being voltage to current driven. The VCCS 142 includes an instrumentation amplifier, voltage follower, and a hardwired 20 kohm resistor. An auxiliary high-pass-filter (HPF) 141 blocks DC voltage from flowing into tissue. The voltage follower, 20 kohm resistor and HPF together ensure that (a) current is controlled and regulated well below hazardous levels, and (b) frequencies are limited above 3.5 kHz to fully comply with IEC-60601 safety guidelines. In this prototype, an AC current of 174 uA (RMS) is injected into the tissue.

In this prototype, the IC(+) electrode 101 and IC(−) electrode 103 inject the AC current into the tissue. The PU(+) electrode 104 and PU(−) electrode 102 pick up the voltage response of the tissue. A voltage-to-current converter (V2CC) 143 includes an operational amplifier and converts the received voltage response to a current signal. The total gain produced by (i) the V2CC 143 and (ii) a reference resistor 144 at input RFB affects the load dynamic range.

In this prototype, an ATmega328P micro-controller 150 controls, and receives impedance measurements from, the AD5933 network analyzer 151, via an I²C (inter-integrated circuit) connection 154. The microcontroller 150 executes certain algorithms, and may assess their performance on an embedded platform. The microcontroller 150 communicates with a computer 120 via a USB connection 155. Alternatively, the microcontroller 150 communicates wirelessly with computer 120.

In this prototype, the IC electrodes and PU electrodes comprise 1" adhesive gel electrodes (Covidien® H124SG). These surface electrodes are advantageous, because they allow non-invasive and precise fixture of the electrodes to the arm. The contact electrolyte gel mitigates the high impedance of the skin at lower frequencies, typically under 1 kHz. Alternatively, the electrolyte gel may be omitted, and the high impedance of the skin at lower frequencies may be mitigated by removing the DC component from the excitation signal. So-called "dry" electrodes may lower the system's cost and improve its unobtrusiveness and reusability and may rely on natural perspiration of the skin.

In this prototype, the IMU 152 is attached to a wristband-like strap and worn on the user's forearm. The IMU 152 streams measurements of the forearm's orientation and displacement. The IMU 152 comprises an MPU9150, which includes a 3-axis accelerometer, a 3-axis gyroscope, and a 3-axis magnetometer in a single chip. In the actual prototype, the IMU chip is positioned on a breakout board and connected to an off-the-shelf Arduino® board with an identical ATMega328P micro-controller. Alternatively, the IMU 152 may be connected to the I²C bus 154 (as shown in FIG. 2), thereby embedding the IMU 152 and EBI spectrometer on a single board.

Prototype Calibration

In this prototype, the EBI and IMU measurements taken during operation are calibrated—that is, adjusted (e.g., scaled or corrected)—based on data acquired during prior calibration steps.

In this prototype, the impedance measurements—real and imaginary 16-bit data words for each exciting frequency— are scaled, based on data acquired during prior calibration. This scaling compensates for the complex impedance introduced by the prototype's electronic components, including between the AD5933 and the studied tissues.

In this prototype, a computer scales the magnitude of each impedance measurement by a gain factor, as follows:

$$|Z_{tissue}(\omega)| = \frac{\text{Magnitude}}{\text{Gain Factor}} = \frac{\sqrt{\mathcal{R}(\omega)^2 + \mathcal{I}(\omega)^2}}{G(\omega)} \qquad \text{Eq. 8}$$

where $\omega$ is angular frequency in radians per second, $Z(\omega)$ is frequency-dependent impedance, $R(\omega)$ is frequency-dependent resistance, $I(\omega)$ is frequency-dependent current, and $G$ is frequency-dependent gain factor.

The frequency dependent gain factor (which is employed for scaling of impedance measurements) is determined during a previous calibration step as follows: During the prior calibration step, a computer calculates the frequency-dependent gain factor for the prototype from an 2R-1C circuit with known impedance (e.g., the $(R_i+C_m)\|R_e$ circuit discussed above).

In this prototype, a computer adjusts the phase angle of each impedance measurement by a system phase offset that is calculated during a previous calibration step. During the prior calibration step, a computer derives the system phase offset of this prototype from a circuit with pure resistance. The system phase $\angle$system($\omega$) offsets the measured impedance as follows:

$$\angle Z_{tissue}(\omega) = \tan^{-1}\left(\frac{\mathcal{I}(\omega)}{\mathcal{R}(\omega)}\right) - \angle\text{system}(\omega) \qquad \text{Eq. 9}$$

where $\angle Z_{tissue}(\omega)$, $R(\omega)$, $I(\omega)$ are the frequency-dependent phase angle, frequency-dependent resistance and frequency-dependent current, respectively for the prototype driving current through the tissue.

In this prototype, the IMU allows programmable full-scale ranges to each of its components. Based on characteristic motion of a human arm, these ranges are set to ±250 degrees per second, ±2 grams, and ±1200 microTesla for the gyroscopes, accelerometer, and magnetometer, respectively.

In this prototype, the nine IMU measurements (from the 3-axis gyroscope, 3-axis accelerometer and 3-axis magnetometer) are scaled and corrected based on data acquired during a previous calibration step. During this previous calibration step, offsets in the angular velocity and linear acceleration are measured with a simple gimbal.

Prototype Feature Extraction

During operation of this prototype, a computer extracts features from calibrated EBI and IMU measurements. Specifically, the features extracted from the calibrated EBI measurements are: circle center ($Y_c$), circle radius (R), infinity impedance ($R_\infty$), static impedance ($R_0$), depression angle ($\alpha$), center frequency ($f_c$), and fit accuracy (Var$\{R_n\}$). The features extracted from the calibrated IMU measurements are four quaternion orientations ($q_0$), ($q_1$), ($q_2$), and ($q_3$).

Prototype Representation of EBI Data with Cole-Cole Model

In this prototype, a computer compactly represents the EBI data with a Cole-Cole model. To calculate the parameters of the Cole-Cole model, a computer maps the calibrated impedance samples to the impedance plane in a Cole-Cole plot. In a Cole-Cole plot, the vertical axis may be imaginary impedance (in ohms) and the horizontal axis may be real impedance (in ohms). Each data point on the impedance plane in a Cole-Cole plot may correspond to the resistance and reactance measured at a single frequency. A computer seeks to fit these points to the Cole equation—a perfect semicircle with the center depressed below the resistance axis.

In this prototype, a computer leverages the circular shape to estimate the parameters of the Cole-Cole model. Instead of solving directly for the model parameters ($R_\infty$, $R_0$, $\tau$, $\alpha$ and $f_c$), the computer estimates the circular curve that best represents the measured impedance data. The computer does so by finding a point ($X_c$,$Y_c$) that minimizes the variance in the distances $R_n$, measured from point ($X_c$,$Y_c$) to the N impedance data points, respectively:

$$\min \text{Var}\{R_n^2\} = \min \text{Var}\{|(X_c,Y_c)-Z_n|^2\} \qquad \text{Eq. 10}$$

In this prototype, a computer treats this point ($X_c$,$Y_c$) as the Cole-Cole model circle center. A computer calculates a closed form solution for such minimization by differentiating Equation 10. The result of this solution is the circle center and its radius. The radius is calculated as being equal to the average distance from the circle center to the data points. The Cole-Cole model parameters, $R_\infty$, $R_0$ and $\alpha$, are solved (by a computer) geometrically from the circle center.

In this prototype, a computer calculates the center frequency $f_c$ as follows: Lengths of cords $u_i$ and $v_i$, which join each impedance data point i with $R_\infty$ and $R_0$, respectively, are calculated. The impedance points are then projected to a $\log(u_i/v_i)$ vs. $\log(\omega_i)$ plane, where they yield a line with slope $(1-\alpha)$. The x-axis intercept of this line determines the center frequency.

In this prototype, a computer may calculate the variance in $R_n^2$, which may be treated as an additional parameter in the EBI data representation. This variance serves as an indicator of how accurately the EBI data fits to a circular curve. This variance may be utilized when performing real-time classification, to identify movement artefacts and discard them.

Prototype Representation of IMU Data

In this prototype, a computer performs an AHRS (Attitude and Heading Reference System) sensor-fusion algorithm to handle the IMU measurements. The algorithm produces a four-vector quaternion representation of the IMU's orientation in 3D space. Specifically, this prototype employs an AHRS sensor fusion algorithm described in S. Madgwick et al., *"Estimation of IMU and MARG orientation using a gradient descent algorithm"*, 2011 *IEEE International Conference on Rehabilitation Robotics*. Advantageously, this AHRS sensor-fusion algorithm is more computationally efficient than Kalman-Filter implementations. The sensor fusion algorithm derives simple gradient descent steps to conduct fusion and estimations iteratively, allowing it to operate on computationally constrained platforms compatible with wearable devices.

Prototype Execution

In this prototype, one or more computers execute the extraction algorithms in real time. The orientation state is updated continuously, processing IMU measurements at a 400 Hz sampling rate. The EBI feature extraction algorithm processes a frequency sweep at a 0.64 Hz rate. The frequency sweep obtains 50 samples equally spaced between 4 kHz and 100 kHz. The frequency resolution may be modified to boost the sweeping rate at the expense of the fit accuracy. The sweeping rate determines the rate at which the feature vectors are generated. The EBI features are first extracted and then extended with the current four-vector quaternion orientation.

In this prototype, the feature extraction algorithms may be executed either by an ATmega328P micro-controller or by a personal computer. Running on the micro-controller reduces dramatically (by a factor of 18) the data to be communicated to the next stage.

In this prototype, the AD5399 network analyzer 151 is housed on the wristband and performs, among other things, DFT (Discrete Fourier Transform) to extract impedance samples out of the picked voltage given the injected current for a specific frequency. The ATmega328P micro-controller 150 is also housed on the wristband and performs, among other things, the following algorithms: (a) calibration and scaling of the impedance measurements; (b) controlling frequency sweeps according to configured range and frequency resolution; (c) Cole-Cole model fit for each frequency sweep; (d) calibration of the nine measurements obtained from the IMU; (e) sensor fusion of the nine measurements to extract four vector quaternions; and (f) communication, streaming features to the personal computer 120.

In this prototype, computer 120 is a local PC (personal computer). Computer 120 performs, among other things, the following algorithms: (a) data labelling and logging during collection mode; (b) training classifiers and choosing the optimal one based on recorded data during enrolment mode; (c) applying a classifier on real time data from the user to detect whether or not the hand is inside the mouth during detection mode; (d) controlling a UI (user interface) to visually display, to the user, information regarding hand orientation and hand-to-mouth classification in real time.

In this prototype, communication from the microcontroller 150 on the wristband to the local PC 120 is done over USB. Alternatively, this communication between the microcontroller 150 and PC 120 may be wireless (e.g., by Bluetooth™ wireless communication).

Prototype Software for Hand-to-Mouth Detection

In this prototype, the sensor system operates in three different modes: (1) collection mode; (2) enrollment mode, and (3) detection mode.

Collection mode logs real-time collected data and extracted features into a local file for later analysis. A human observer labels the data with a binary label. Positive and negative labels correspond to situations when the hand is inside and outside the mouth.

Enrollment mode accepts previously collected labeled data either from a specific user or a group of users. It optimizes a set of machine-learning algorithms and chooses the one that is most likely to perform best.

In detection mode, the system detects the hand's situation (e.g., whether or not hand-to-mouth behavior is occurring) in real time. In detection mode, the algorithm estimates, based on the features vector, whether or not the hand is in the mouth. The detected hand situation and the arm's orientation are visually displayed to the user as feedback.

Loosely speaking: (a) during enrollment mode, the system "bakes" into the algorithm the knowledge of what in and out of the mouth looks like; and (b) then in detection mode the system applies this knowledge.

In this prototype, a computer is programmed to perform classification, using Scikit-Learn® algorithms for five classification models: Random Forests (RF), Support Vector Machines (SVM), AdaBoost (AB), K-Nearest Neighbours (KNN) and Logistic Regression (LR). The models differ in their underlying statistical assumptions and algorithmic implementations. Hence, they differ not only in the accuracy they may achieve, but also in the computational complexity their training or detection involve.

In this prototype, a computer optimizes the unique parameters of the classification models, by searching a grid of possible values. A classifier instance is trained for each parameter combination. How well it generalizes is assessed using 3-iteration random subsampling cross-validation. Once the optimal parameters per classification model are set, a computer may select, from among the models, based on their mean validation accuracy.

In this prototype, detection mode includes two mechanisms to facilitate the real-time detection and feedback. First, it discards data points whose Cole-Cole circular fit accuracy is below a threshold (i.e. high $Var\{R_n^2\}$). These were observed during natural movement, in singular cases— when by the time a frequency sweep is over, the user has already changed between postures with different EBI spectra. The motivation for discarding the data points is that fitting to the inconsistent measurements does not truthfully represent points with a binary label. Discarding them, therefore, prevents unnecessary detection errors. Second, a moving average window on the detection labels was implemented, smoothing the visual feedback presented to the user.

In this prototype, classification is performed by any combination of five classification models: RF, SVM, AB, KNN and LR. Alternatively, any binary-classification model that implements a fit, score and predict interface may be employed.

Prototype Evaluation: Body Position

A first experiment was performed using this prototype, to determine how hand-to-mouth behaviors manifest in the measured EBI spectra. This first experiment was conducted with a single subject in an indoor working environment. The subject wore the device for five consecutive hours, and data was recorded as he naturally moved in this everyday setting. Periodically, the subject was asked to place any of his five fingers in his mouth. An external observer annotated the recorded data with the subject's activity and body postures. Throughout this first experiment, the electrodes were placed in a single configuration (10,1) on the subject's forearm, as described below.

In this first experiment, noticeable differences in EBI recordings were observed between situations where the subject's hand was inside or outside the mouth. These differences occurred at many frequencies in the spectrum of exciting frequencies. When the measured spectra are fitted to a Cole-Cole model, differences (between situations where the subject's hand was inside or outside of the mouth) occurred in many of the Cole-Cole model's parameters. For example, in the first experiment, a mean difference of 32% was observed between static impedance $R_0$ for (i) a sitting posture with the hand outside the mouth and (ii) for the thumb inside the mouth. Similarly, in the first experiment, a mean difference of 5% was observed between center frequency $f_c$ for (i) standing with the hand outside the mouth and (ii) sucking the index finger.

In this first experiment, EBI measurements were taken while the subject was in ten different body postures: (a) the first five body postures comprise inserting fingers one to five, respectively, into the mouth; and (b) the other five body postures comprise (i) crossing the arms, (ii) clasping the hands, (iii) leaning the head on a hand, (iv) sitting, and (v) standing. In the latter five body positions, the fingers are not in the mouth.

In this first experiment, the EBI spectrum generated by clasping the hands resembles the ones generated by placing any finger inside the mouth. In some instances, clasping the hands produced a circular spectrum that is similar to a spectrum from a hand-to-mouth posture. In that cases, differences in the IMU orientation components settle these ambiguities.

In this first experiment, classification models were trained (as discussed below) for three cases: including only the IMU orientation components, only the EBI components, or both IMU and EBI components. Then the detection accuracies of the trained classification models were assessed, by repeating the first experiment with the same subject on a different day. Detection accuracies of 74.39%, 90.74% and 95.76% were obtained for each of the three cases, respectively (i.e., IMU only, EBI only, or both IMU and EBI). These measured detection accuracies indicate that both the IMU and EBI sensors are well-suited for detecting hand-to-mouth behavior and that the combination of both IMU and EBI is more accurate than either of them alone.

In this first experiment, three postures generated the highest diversity in their corresponding EBI spectra: crossing the arms, clasping the hands, and leaning the head on the hand. In this first experiment, two postures had the highest rate of occurrence in the dataset: sitting and standing.

Prototype Evaluation: Electrode Position

A second experiment studied the effect of positioning the electrodes for this prototype at different locations on the forearm.

Figure 3A:
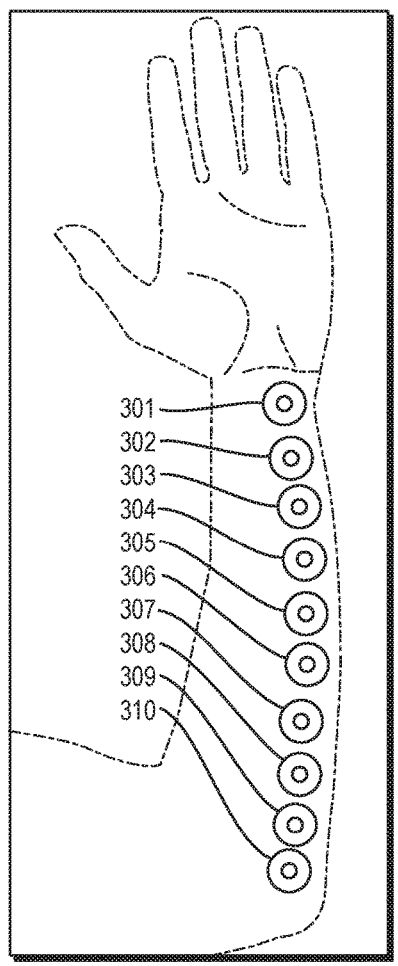
FIGS. 3A and 3B show electrode positions that were tested in a prototype of this invention, four electrodes at a given time.
Figure 3B:
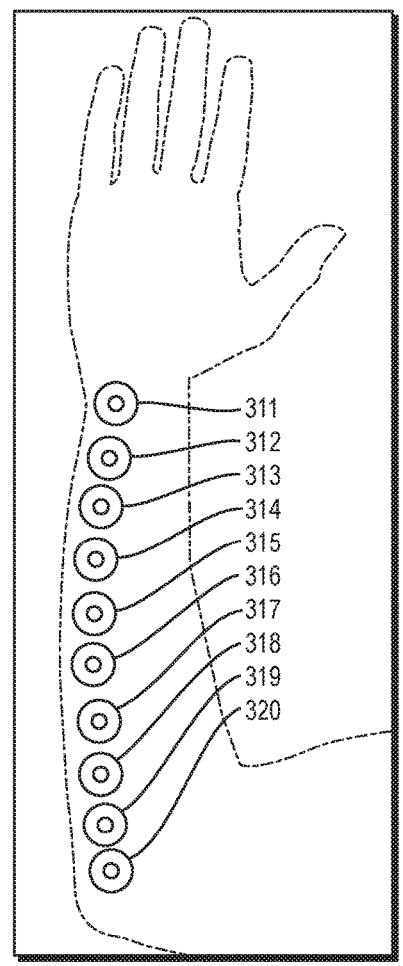

FIGS. 3A and 3B show electrode positions that were tested in the second experiment, four electrodes at a given time. In the second experiment, a total of twenty electrodes 301-320 for this prototype were arranged in two rows on the subject's forearm, as shown in FIG. 3A and FIG. 3B. FIGS. 3A and 3B show views of the anterior side and posterior side, respectively, of the same forearm of the subject. In FIG. 3A, a first row of ten electrodes 301, 302, 303, 304, 305, 306, 307, 308, 309, 310 are attached to the skin of the anterior side of the forearm. In FIG. 3B, a second row of ten electrodes 311, 312, 313, 314, 315, 316, 317, 318, 319, 320 are attached to the skin of the posterior side of the forearm. In this first experiment, the mean distance between the center of consecutive electrodes was 2.66 cm.

The following terminology is sometimes used herein to describe the position of the electrodes: The ten electrodes on the anterior side are sometimes referred to herein as "L" electrodes. The ten electrodes on the posterior side are sometimes referred to herein as "R" electrodes. The positions of the electrodes along a proximal-distal axis are indexed from position one to position ten, with position one being the most proximal closest to the elbow and position ten being the most distal closest to the wrist. For example, electrode 310 is an L electrode at position one; and electrode 311 is a R electrode at position ten.

As used herein, the electrodes' position in this index may denote their configuration. For example, in configuration (10,1), the IC(+) and PU(+) electrodes are at position ten and the IC(−) and PU(−) electrodes are at position one. Also, for example, in configuration (6,5), the IC(+) and PU(+) electrodes are at position six and the IC(−) and PU(−) electrodes are at position five. As used herein, a number that immediately follows the word "position" is not a reference number for a patent drawing.

In the second experiment, only four of the twenty electrodes were employed at any given time, two IC (inject current) electrodes and two PU (pick-up) electrodes. The PU and the IC electrodes were positioned in a crossed alignment, in which the current density fields intersect each other.

In the second experiment, the prototype took EBI measurements at different electrode positions. The distance between the (+) and (−) electrodes, as well as their position along the forearm, was varied, and EBI measurements were taken at each of the different configurations. Specifically, the positions of the electrodes were varied by:

(a) moving the (+) pair towards the elbow—from configuration (10,1) to (2,1), one configuration at a time, taking EBI measurements for each configuration—that is, taking EBI measurements for configurations (10,1), (9,1), (8,1), (7,1), (6,1), (5,1), (4,1), (3,1), (2,1), respectively;

(b) moving the (−) pair towards the wrist—from configuration (10,1) to (10,9), one configuration at a time, taking EBI measurements for each configuration—that is, taking EBI measurements for configurations (10,1), (10,2), (10,3), (10,4), (10,5), (10,6), (10,7), (10,8), (10,9), respectively; and (c) symmetrically moving both pairs towards each other—from configuration (10,1) to (6,5), one configuration at a time, taking EBI measurements for each configuration—that is, taking EBI measurements for configurations (10,1), (9,2), (8,3), (7,4), (6,5), respectively.

In the second experiment, each electrode configuration was evaluated by two separate metrics: (a) sensitivity to changes around the fingers; and (b) detection accuracy.

In the second experiment, to assess electrode configurations based on their sensitivity to changes in EBI, a computer calculated fluctuations in measured impedance that occur as the fingers touch different body parts. The more intense the fluctuations were, the more conductivity changes around the fingers contributed to the overall impedance. Samples were taken for each of the ten different body postures described above. For each electrode configuration, an identical number of samples were recorded for each of these ten body postures. Fluctuations were calculated by determining the coefficient of variation for the impedance magnitude in the recording:

$$\text{Coefficient of variation} = \frac{std\{|Z|\}}{mean\{|Z|\}} \quad \text{Eq. 11}$$

In the second experiment, to assess electrode configurations by their detection accuracy, an additional recording session was held with the same subject on a different day and his arm re-instrumented with the electrodes. The EBI spectra for the various body postures in this additional session served as an independent test set. In this second experiment, only the EBI features were used, and the IMU orientation components were discarded. This way, EBI results only reflected the electrical dissimilarities between the electrode configurations. A classification model was trained and its optimal parameters were selected, using data only from a first recording session. The electrode configurations were compared with their detection accuracy on the test set.

According to the test results for the second experiment: The coefficient of variation gradually increases as the electrodes in the pairs move further from each other. The further apart the electrodes are, the further the current density fields spread inside the tissue, causing distant regions, such as around the fingers, to have a higher relative contribution to the overall impedance. Furthermore, the coefficient of variation may be affected by which region is between the electrodes. Specifically, the coefficient of variation is higher when the region between the electrodes is closer to the wrist rather than the elbow.

According to the test results for the second experiment, configuration (10,1) yields powerful accuracy results as anticipated by its coefficient of variation. Nonetheless, the best accuracy results (up to 97.6%) are produced by configuration (6,5). The configuration (6,5) is more compact than configurations in which electrodes are further apart, and thus may be advantageous for wearable applications.

The four electrodes for the prototype are, in many use scenarios, positioned in a crossed arrangement. A crossed arrangement may be advantageous for at least two reasons. First, unlike a conventional parallel arrangement of electrodes (which is designed to detect changes in EBI in a region surrounded by the electrodes), the crossed arrangement of electrodes is well suited to sense changes in EBI further away, such as in regions outside of the forearm which are electrically coupled by the touch of the fingers. The crossed arrangement tends to nullify the sensitivity field (dot product) inside the forearm by creating antiparallel components between the current density fields. Also, the crossed arrangement tends to increase sensitivity further away from the electrodes, where the fields become more parallel.

Figure 4:
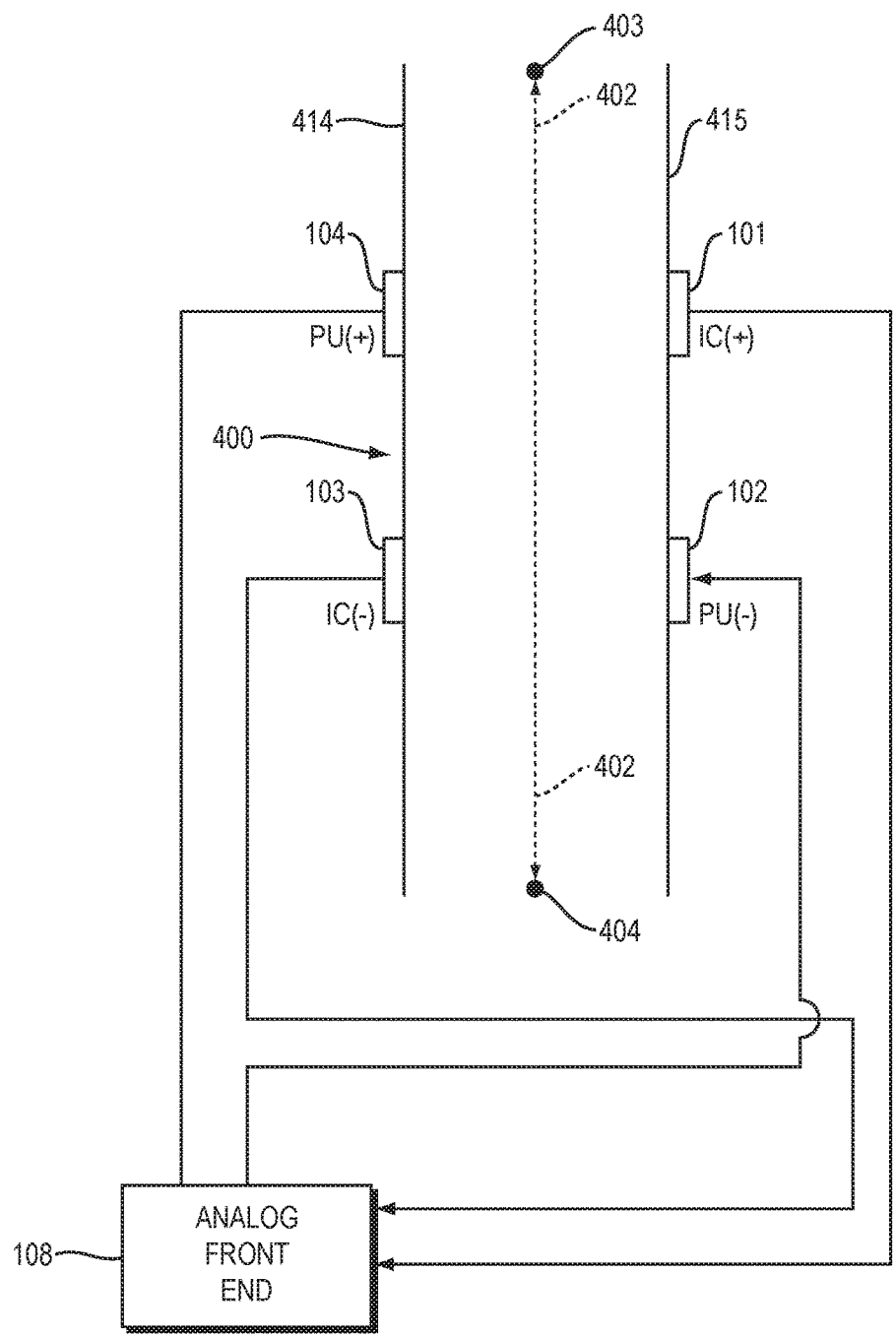
FIG. 4 illustrates a crossed alignment of electrodes.

FIG. 4 illustrates a crossed arrangement of electrodes. In this crossed arrangement, an IC electrode and a PU electrode are attached to the anterior side 414 of the forearm 400, and the other IC electrode and the other PU electrode are attached to the posterior side 415 of the forearm 400. In the example of a crossed arrangement shown in FIG. 4: (a) the IC(+) electrode 101 and the PU(−) electrode 102 are located in the R band on the posterior side 415 of the forearm; and (b) the IC(−) electrode 103 and the PU(+) electrode 104 are located in the L band on the anterior side 414 of the forearm. Furthermore, in FIG. 4, the crossed electrodes are spatially arranged such that a first plane intersects a second plane, where: (a) the first plane is a geometric plane that intersects both of the IC electrodes 101, 103; (b) the second plane is a geometric plane that intersects both of the PU electrodes 102, 104; and (c) a geometric line that lies entirely in the first plane and a geometric line that lies entirely in the second plane are each perpendicular to a proximal-distal axis 402 of the forearm. The proximal-distal axis 402 intersects the wrist 403 and elbow 404.

A third experiment for the prototype tested the effect of crossed electrodes, in a prototype of this invention. In this third experiment, a crossed arrangement of four electrodes performed best for sensing conductivity changes around the wearer's fingers—further away from the electrodes themselves and the volume they circumscribe. The crossed arrangement of electrodes tended to cause a higher coefficient of variation and higher classification accuracies than other electrodes in a traditional, parallel arrangement.

Specifically, in this third experiment, the crossed arrangement of electrodes was compared to a traditional, parallel arrangement of electrodes. In the traditional arrangement, the four electrodes were positioned to generate parallel current density fields inside a region between the electrodes.

In this third experiment, EBI measurements were taken with a crossed arrangement of electrodes. EBI measurements were also taken with electrodes in a traditional, parallel arrangement of electrodes. This parallel arrangement was created by: (a) placing the IC(+) and IC(−) electrodes on the L band in position ten and position one respectively; and (b) placing the PU(+) and PU(−) electrodes on the R band in position ten and position one respectively.

As noted above, FIG. 4 shows an example of a crossed arrangement of electrodes. However, if the positions of PU(−) electrode 102 and IC(−) electrode 103 were interchanged in FIG. 4, this would result in an example of a traditional, parallel arrangement of electrodes.

In the third experiment, the crossed arrangement of electrodes outperformed the traditional, parallel arrangement of electrodes. Specifically, the classification accuracy for the traditional, parallel arrangement of electrodes was 78.16%; whereas the detection accuracy for the crossed arrangement of electrodes was 92.55%, all other things being equal (e.g., using the same classification algorithm). Furthermore, the coefficient of variation for the traditional, parallel arrangement of electrodes was 0.62; whereas the coefficient of variation for the crossed arrangement of electrodes was over 2, all other things being equal (e.g., using the same classification algorithm). The higher coefficient of variation for the crossed electrodes indicates that the crossed electrodes are more sensitive to EBI changes caused by the different body postures.

Figure 5A:
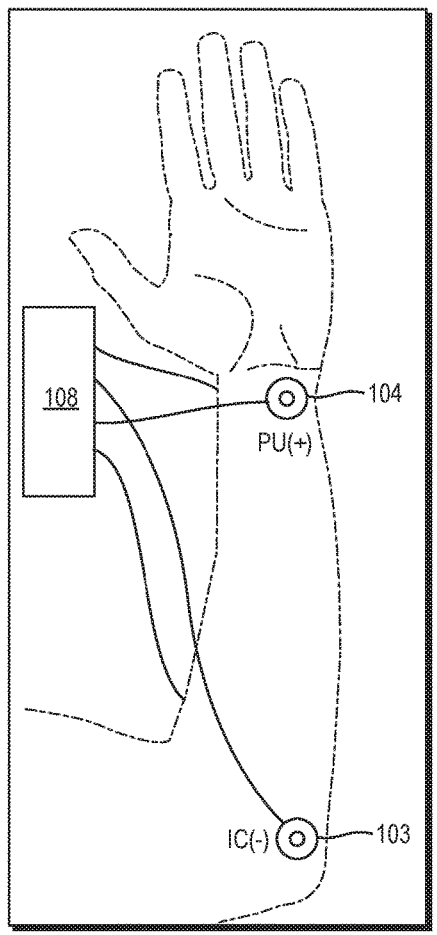
FIG. 5A and FIG. 5B show four crossed electrodes in a (10,1) configuration. Out of these four crossed electrodes, two are attached to the anterior side of the forearm and are shown in FIG. 5A, and the other two are attached to the posterior side of the forearm and are shown in FIG. 5B.
Figure 5B:
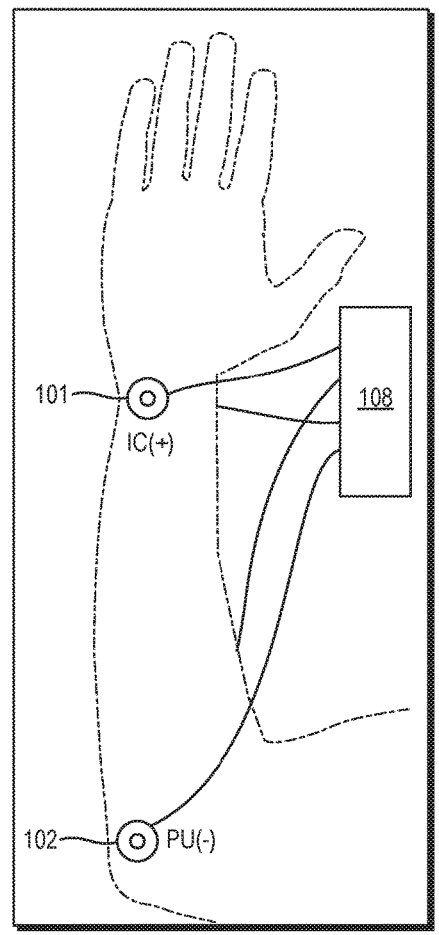

FIG. 5A and FIG. 5B show four crossed electrodes in a (10,1) configuration, in an illustrative implementation of this invention. Out of these four crossed electrodes, two are attached to the anterior side of the forearm and are shown in FIG. 5A, and the other two are attached to the posterior side of the forearm and are shown in FIG. 5B.

In FIGS. 5A and 5B, the (+) electrodes are at position ten, and the (−) electrodes are at position one. Specifically, in FIGS. 5A and 5B, IC(+) electrode 101 and PU(+) electrode 104 are each at position ten (closest to the wrist), and IC(−) electrode 103 and PU(−) electrode 102 are each at position one (closest to the elbow).

Figure 6A:
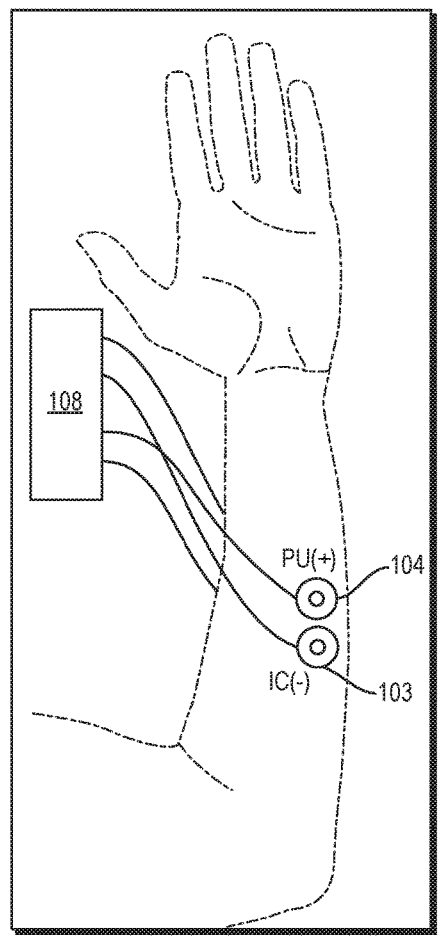
FIG. 6A and FIG. 6B show four crossed electrodes in a (6,5) configuration. Out of these four crossed electrodes, two are attached to the anterior side of the forearm and are shown in FIG. 6A, and the other two are attached to the posterior side of the forearm and are shown in FIG. 6B.
Figure 6B:
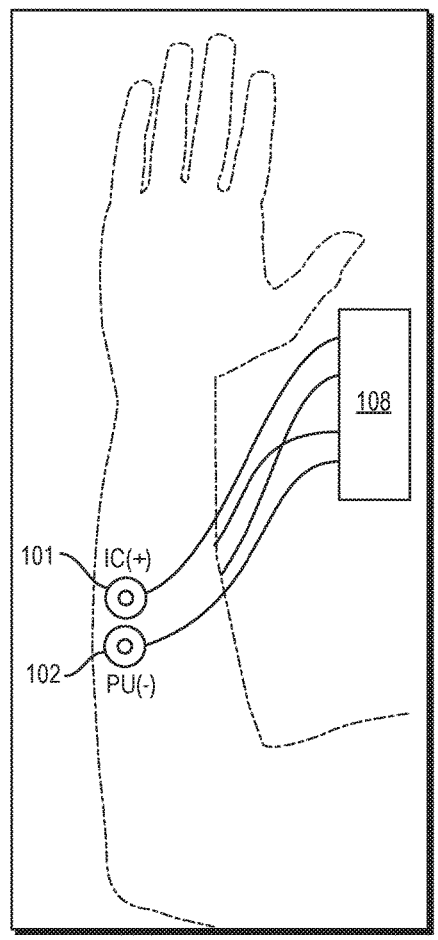

FIG. 6A and FIG. 6B show four crossed electrodes in a (6,5) configuration, in an illustrative implementation of this invention. Out of these four crossed electrodes, two are attached to the anterior side of the forearm and are shown in FIG. 6A, and the other two are attached to the posterior side of the forearm and are shown in FIG. 6B.

In FIGS. 6A and 6B, the (+) electrodes are at position six, and the (−) electrodes are at position five. Specifically, in FIGS. 6A and 5B, IC(+) electrode 101 and PU(+) electrode 104 are each at position six (near the middle of the forearm, along the proximal-distal axis), and IC(−) electrode 103 and PU(−) electrode 102 are each at position five (near the middle of the forearm, along the proximal-distal axis).

In each of FIGS. 5A and 6A, two of the crossed electrodes are visible. Specifically, the PU(+) electrode 104 and IC(−) electrode 103 are visible, since they are attached to skin on the anterior side of the forearm. However, the other two electrodes in the crossed electrodes are in hidden view, since they are attached to skin on the posterior side of the forearm.

In each of FIGS. 5B and 6B, two of the crossed electrodes are visible. Specifically, the PU(−) electrode 102 and IC(+) electrode 101 are visible, since they are attached to skin on the posterior side of the forearm. However, the other two electrodes in the crossed electrodes are in hidden view, since they are attached to skin on the anterior side of the forearm.

Prototype Evaluation: Multiple Usage

A fourth experiment analyzed aspects of the prototype's robustness, using data collected from one or more subjects on multiple days. The fourth experiment assessed two use cases: (1) recurrent usage by the same user and (2) encountering previously unseen users for the first time.

The first use case is when the same user wears the prototype on separate days. This captures imprecisions that may occur during recurrent usage of the system, such as inconsistent placement of the electrodes or misalignment of the IMU. Additionally, it accounts for transient changes in bioelectrical properties of the wearer's forearm. These may introduce perturbations of over 8% in an EBI spectrum. They are likely to stem from temporal variations in fluid volumes, blood pressure, body temperature, nervous activity, hydration, electro-dermal activity, et cetera.

The second use case assesses how well the prototype generalizes, performing on new subjects that have not been previously seen. This tests the prototype's tolerance to person-to-person differences, including differences in adipose, muscle and vasculature ratios, bone anatomy, subdermal water content and skin thickness.

Fifteen subjects, 8 females and 7 males, were recruited to participate in the fourth experiment. All subjects were between the ages 21 and 33 (mean=26.5; σ=3.6). Their forearm length was measured and ranged between 22 cm and 27.5 cm (mean=24.8; σ=1.7). They were asked for their weight, which varied between 47 kilograms and 77 kilograms (mean=58.3; σ=9.4), and their height which varied between 155 cm and 185 cm (mean=169; σ=8.9).

In order to test the second use case, the subjects attended identical sessions on two separate days over the course of a single month. Each subject attended two sessions on different days. Each of these sessions had two parts. In the first part of each session, measurements were taken with electrodes in configuration (10,1). In the second part of each session, measurements were taken with electrodes in configuration (6,5). The reason for the second session was to evaluate detection accuracy. The data from the first meeting was used to train the algorithms. The data from the second meeting was used to evaluate detection accuracy. The subjects' forearm length was measured, and the placement of each electrode within the combination was scaled accordingly. Data were recorded as the subjects were asked to pose in the ten body postures discussed above. Positive and negative labels were assigned to postures when a subject's hand was inside or outside the subject's mouth, respectively.

An additional subtlety was introduced for postures in which the hand was placed inside the mouth. For each finger, measurements were taken both when the finger was fully sucked (up to the middle phalanx) and when its tip was only lightly touching the inner lip. This extension simulates dissimilarities between thumb sucking and nail biting, and verifies the system's ability to detect both.

For the fourth experiment, the evaluation is framed as a binary-classification problem, and the system's detection performance may be described in terms of classification accuracy. According to the evaluated use case, the dataset was partitioned for training, validation and testing purposes. Prior to analysis, all data points were scaled using feature standardization.

In the fourth experiment, 10,483 data points were collected, each of which is a Cole-Cole representation of an EBI spectrum, comprising 50 complex impedance measurements, and a corresponding orientation. In the fourth experiment, 6,348 of the data points had a positive label and 4,134 had a negative one.

The first use scenario that was assessed in the fourth experiment is when the same individual recurrently wears the prototype. In this first use scenario, a classifier is customized per user, as follows: The first recording session is randomly partitioned into training and validation datasets. Data recorded in the second session is held out as a test set. The parameter space of each classification model is searched. The combination of classification algorithm and parameters, which optimizes the performance on the validation set, is selected as the subject's personal classifier.

Table 1 reports the median, average and standard deviation of the test accuracy scores obtained by the personal classifiers. It shows that when recurrently worn by the same user, the prototype achieves a median accuracy of up to 92.95%, detecting hand-to-mouth behaviors. Encouragingly, electrode configuration (6,5) performed equally well as configuration (10,1). The median statistic is relevant, as it is the most robust to subjects which are potentially outliers in our user base.

Another part of the fourth experiment also assessed the effect of: (a) training the personal classifiers only with a specific classification model (rather than selecting the optimal classification model for the user); and (b) only optimizing the parameters of the specific classification model per user. For configuration (10,1), similar median accuracies were obtained when using only KNN classifiers and when optimizing with all possible models. The same emerges for configuration (6,5), training only on RF classifiers. Thus, in some cases, it is desirable to train using only a single classification model.

Table 1 below summarizes detection accuracies for recurrent usage by the same user. For Table 1, baseline accuracies were generated by a stratified dummy classifier.

TABLE 1

| Config. | Classifier | Test accuracies | |
| --- | --- | --- | --- |
| | | Median | Mean (σ) |
| (10.1) | Optimal | 92.95% | 90.98% (6.3) |
| | KNN | 92.15% | 88.31% (6.5) |
| | Baseline | 53.42% | 53.4% (3.3) |
| (6.5) | Optimal | 91.6% | 90.96% (7.1) |
| | RF | 91.6% | 85.47% (9.2) |
| | Baseline | 53.83% | 52.9% (3.2) |

The fourth experiment also assessed the prototype's performance in a second use scenario, when encountering subjects that it has not previously seen. To assess this use scenario, the dataset was partitioned, holding-out data points from 3 subjects (20%) for testing purposes. The remaining subjects were used for training and validation. Data points were measured for each subject (i.e. person) for each of the two recording sessions. This diversified the dataset with multiple usages. The optimal combination of classification model and parameters was selected by its validation accuracy. Each combination's test accuracy was assessed based on detection of hand-to-mouth behavior, made by that combination, for the previously unseen test subjects.

Table 2 reports the median, average and standard deviation of the test accuracies obtained by the optimal classifiers. The results reported in Table 2 indicate that the prototype is likely to produce an accuracy of 87.5%, detecting hand-to-mouth behaviors for subjects it has never before seen. In Table 2, these high accuracy results were produced for electrode configuration (10,1). For two thirds of the subjects' assignments, RF was selected as the optimal model regardless of the electrode configuration. This indicates that the RF model may be the best one for this kind of task.

The fourth experiment also assessed adjusting the classifiers by the users' physicality. The subjects were divided into two groups, based on their physical gender, age, weight, height and forearm length. A 2-component Gaussian Mixture Model clustering technique was used, utilizing Expectation Minimization (EM) to fit the subjects' physicality measurements. Except for a single subject, the resulting clusters overlapped with the subjects' physical genders. The clusters were marked F and M respectively, according to the majority of females and males in their population.

The analysis described above for the second use scenario (usage by multiple subjects) was repeated for each of the clusters separately. To preserve the ratio from the former analysis, a single subject was held-out for testing from the M cluster, and a pair were held-out from cluster F. The median, mean and standard deviations of the test accuracies are also presented in Table 2 for comparison.

TABLE 2

| Config. | Dataset | Test accuracies | |
| --- | --- | --- | --- |
| | | Median | Mean (σ) |
| (10.1) | All | 87.5% | 87.21% (5.1) |
| | Cluster F | 90.52% | 87.96% (6.3) |
| | Cluster M | 90.72% | 88.14% (6.1) |
| (6.5) | All | 79.69% | 79.81% (5.5) |
| | Cluster F | 83.25% | 84.7% (7.9) |
| | Cluster M | 82.09% | 82.82% (4.4) |

Successful improvements of up to 3% in the median accuracies were observed employing this approach (i.e., adjusting classification parameters based on the subject's physicality). Thus, in some implementations, person-to-person differences may be ameliorated by an a priori query of the user's physicality. For example, multiple classifiers may be optimized based on physical typecasts. A mixture of those may then be employed for unseen users, consequently improving expected accuracy. The mixture may be weighted by the users' similarity to the physical typecasts produced while training.

Flow Charts

Figure 7:
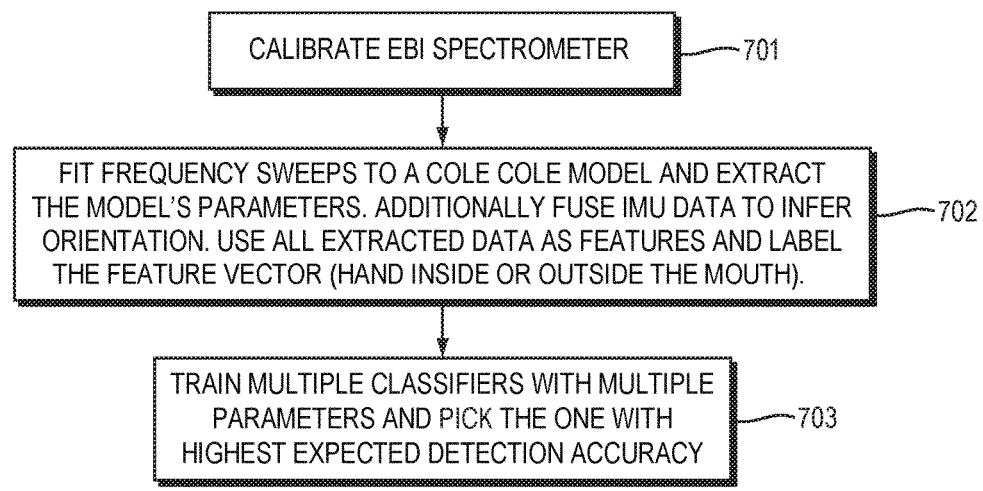
FIG. 7 is a flow chart of calibration steps.

FIG. 7 is a flow chart of a calibration method, in an illustrative implementation of this invention. In the example shown in FIG. 7, the method includes the following steps: Step 701: Calibrate EBI spectrometer. Step 702: Fit frequency sweeps to a Cole Cole model and extract the model's parameters. Additionally fuse IMU data to infer orientation. Use all extracted data as features and label the feature vector (hand inside or outside the mouth). Step 703: Train multiple classifiers with multiple parameters and pick the one with highest expected detection accuracy).

Figure 8:
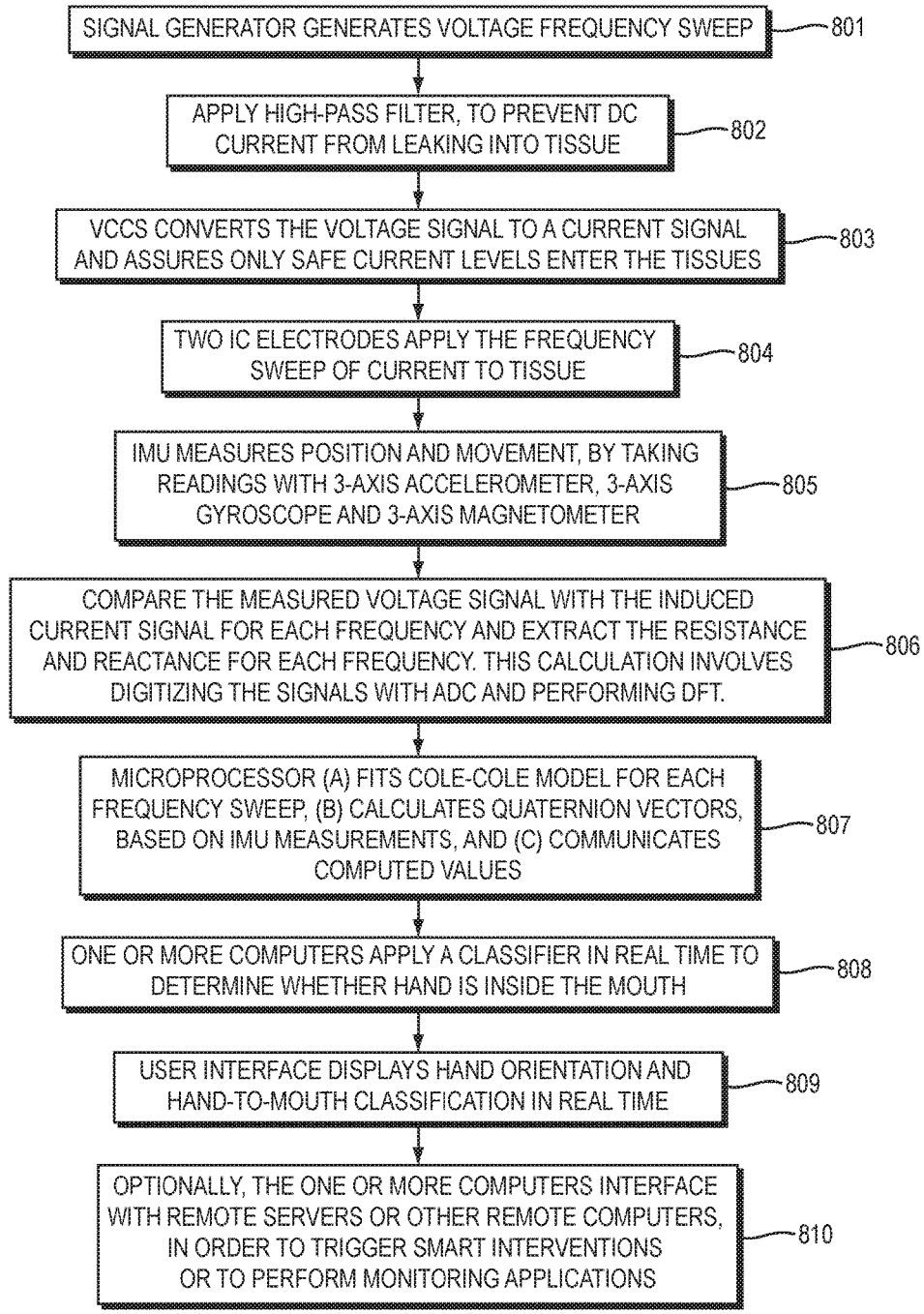
FIG. 8 is a flow chart of a method for detecting hand-to-mouth behavior.

FIG. 8 is a flow chart of a method for detecting hand-to-mouth behavior, in an illustrative implementation of this invention. In the example shown in FIG. 8, the method includes the following steps: Step 801: Signal generator generates voltage frequency sweep. Step 802: Apply high-pass filter, to prevent dc current from leaking into tissue. Step 803: VCCS converts the voltage signal to a current signal and assures only safe current levels enter the tissues. Step 804: Two IC electrodes apply the frequency sweep of current to tissue. Step 805: IMU measures position and movement, by taking readings with 3-axis accelerometer, 3-axis gyroscope and 3-axis magnetometer. Step 806: Compare the measured voltage signal with the induced current signal for each frequency and extract the resistance and reactance for each frequency. This calculation involves digitizing the signals with ADC and performing DFT.

Step 807: Microprocessor (a) fits Cole-Cole model for each frequency sweep, (b) calculates quaternion vectors, based on IMU measurements, and (c) communicates computed values to one or more computers. Step 808: The one or more computers apply a classifier in real time to determine whether hand is inside the mouth. Step 809: User interface displays hand orientation and hand-to-mouth classification in real time. Step 810: Optionally, the one or more computers interface with remote servers or other remote computers, in order to trigger smart interventions or to perform monitoring applications.

Prototype: Source Code

In the Computer Program Listing above, seventeen computer program files are listed. These seventeen computer program files comprise software employed in a prototype implementation of this invention. To run these as Python™ software files, the filename extension for each would be changed from ".txt" to an appropriate Python™ filename extension. Here is a description of these seventeen text files:

(1) RT_receiver.txt: The RT_receiver module is the main entry point for the software for this prototype. This module may be executed using the command line to either collect data or classify data in real time based on a loaded classifier. When executing the module from the command line the following parameters are enabled: (a) output_file_prefix; (b) p [seconds]; (c) no-imu; and (d) train. The output_file_prefix parameter is a prefix that is added to all the collected files so they may be later identified. The p [seconds] parameter is the sampling period. The module will pause sampling every X seconds to allow the user to change pose. If not stated sampling will be continuous. The no-imu parameter specifies that the module should not collect IMU data via the serial port. This is used for a scenario in which only EBI data is collected. The train parameter specifies the mode in which the module should run, i.e. only logging data for training or classifying collected data in real time.

Once the module is executed it launches a Python™ Twisted reactor that connects and initialize all relevant inputs. This includes the EBI board, the IMU, and the observer terminal through which data may be annotated. To annotate data the user inputs the strings "IN" or "OUT" for when a wearer hand is inside and outside their mouth.

The class IMU protocol handles in real-time data from the IMU board. It parses incoming data, scales it, bias it according to previous calibration and estimates quaternions using a sensor fusion algorithm.

The class EBI protocol handles in real time bio-impedance data coming in from the EBI board. It parses the incoming data, compute its magnitude and phase, calibrate it and fits it to a Cole-Cole model. Parameters from the fitted Cole-Cole model are added to the quaternions to create the full feature set. These are either logged or fed to the classifier to detect whether or not the hand is inside the mouth.

(2) Adaboost_classifier.txt: The Adaboost_classifier module implements hand-to-mouth classification using the Adaboost classification algorithm. The module trains a classifier based on an input dataset and a set of algorithm parameters. Then it uses the trained classifier to classify new data points. The module also exports functions which allow searching the space of parameters used by the algorithm. Supported parameters are the number of decision stumps used by the Adaboost algorithm. By searching the space of parameters, the module facilitates selecting the optimal classifier for the problem, based on a cross validation criterion.

(3) AHRS.txt: The AHRS module implements a sensor fusion algorithm which estimates quaternions from nine acceleration, gyroscope and magnetometer data points. This module employs straight forward and iterative calculations, allowing computational efficiency.

(4) AHRS_tester.txt: The AHRS_tester module provides the user with visual feedback regarding the user's arm orientation and whether or not the user's hand is detected to be inside their mouth. Real-time data is streamed to this module from the system's main entry point. The arm orientation is visualized by moving around a 3D object in space in accordance with the wearer's arm. The object changes its color from blue to red whenever the system estimates that the wearer's hand is inside the wearer's mouth.

(5) Classification.txt: The Classification module manages classification. It defines a classifier base-class that different classification algorithms may extend and implement. The base-class implements a set of techniques that allow evaluating and optimizing the classification algorithms. For instance, it allows a classification algorithm to rank the features using feature selection.

(6) ColeColeParameterEstimation.txt: The ColeColeParameterEstimation module implements Cole-Cole parameter estimation, fitting EBI data to a Cole-Cole model. The module receives as input calibrated bio-impedance frequency sweeps, each of which contains a list of data points. The data points correspond to real and imaginary impedance obtained for every frequency in the measured range. The module fits the data points to a circle on the complex impedance plane. It does so by calculating the closed form solution of finding a point on the plane whose distance to all other points is minimal. This point is the circle's center. Then the module computes the circle radius, its intersections with the X axis, and the circle's depression angle under the X axis. The center frequency, which corresponds with the circle's maximal imaginary point, is also calculated and added to the set of model parameters. Then the module computes the fit variance, quantifying how close is the fit.

(7) DatasetsManager.txt: The DatasetsManager module is responsible for managing the datasets for the hand-to-mouth classification task. It provides broad functionality, such as: (a) loading single or multiple feature files and aggregating data points to a single dataset (which may, for example, facilitate creating a training dataset containing only a subset of the study participants); (b) Z-scoring each point in a dataset based on global mean and standard deviation; (c) partitioning a data set to a training set and validation set (e.g., by random select and stratified random select techniques, to cause the resulting partitions to better generalize); and (d) dimensionality reduction and feature selection functionality (for example, to compare classification using a feature set and classification using raw data).

(8) EBI_offline_viewer.txt: The EBI_offline_viewer module is used to visualize EBI data (e.g., for characterization purposes). It loads bio-impedance data, plots it on the complex plane, fits it to a Cole-Cole model and overlays the resulting circle on the same plot.

(9) Electrode_configuration_analysis.txt: The Electrode_configuration_analysis module analyzes classification accuracy for different electrode classifications. Some of the functions in this module analyze, for instance, the accuracy results obtained by the different classifiers. Additional analysis metrics such as the coefficient of variation, were implemented in different modules.

(10) GMM_classifier.txt: The GMM_classifier module implements hand-to-mouth classification using a Gaussian Mixture Models classification algorithm. The module trains a classifier based on an input dataset and a set of algorithm parameters. Then it uses the trained classifier to classify new data points. The module also exports functions which facilitate searching the space of parameters used by the algorithm. Supported parameters are the number of Gaussians in the mixture and the type of covariance matrix that each of which may have. By searching the space of parameters, the module facilitates selecting the optimal classifier for the problem, based on a cross validation criterion.

(11) KNN_classifier.txt: The KNN_classifier module implements hand-to-mouth classification using a K nearest neighbors classification algorithm. The module trains a classifier based on an input dataset and a set of algorithm parameters. Then it uses the trained classifier to classify new data points. The module also exports functions which allow searching the space of parameters used by the algorithm. Supported parameters are the number of neighbors, the distance metric, the leaf size and the p value. By searching the space of parameters, the module facilitates selecting the optimal classifier for the problem, based on a cross validation criterion.

(12) LogisticRegression.txt: The LogisticRegression module implements hand-to-mouth classification using a Logistic Regression classification algorithm. The module trains a classifier based on an input dataset and a set of algorithm parameters. Then it uses the trained classifier to classify new data points, optionally in real-time. The module also exports functions which facilitate searching the space of parameters used by the algorithm. Supported parameters are the slack penalization constant C and the penalty metric (either L1 or L2). By searching the space of parameters, the module facilitates selecting the optimal classifier for the problem, based on a cross validation criterion.

(13) MultipleAlgClassifier.txt: The MultipleAlgClassifier module assists in selecting the optimal classifier among the various classification algorithms. For each of the classifier algorithm the module invokes a parameter search finding the algorithm's optimal set of parameters on the validation set. Then, based on the validation results, the module selects the best algorithm for the particular classification task. This combination of optimal algorithm and parameters may then be used to evaluate the classification accuracy on the test set.

(14) RandomForest_classifier.txt: The RandomForest_ classifier module implements hand-to-mouth classification using a Random Forests classification algorithm. The module trains a classifier based on an input dataset and a set of algorithm parameters. Then it uses the trained classifier to classify new data points, optionally in real-time. The module also exports functions which facilitate searching the space of parameters used by the algorithm. Supported parameters are the number of decision trees to use and the split criterion that the trees use making their decisions. By searching the space of parameters, the module facilitates selecting the optimal classifier for the problem, based on a cross validation criterion.

(15) RT_EBIScaler.txt: The RT_EBIScaler module scales and calibrates the bio-impedance measurements coming in from the EBI board. Calibration data is loaded from a predefined calibration file, which contains frequency sweep measurements from a test circuit with known resistance and capacitance. Using the calibration data, the gain factor and bias are computed. These are then used to scale new measurements received from the EBI board. The module converts impedance measurements to their phase-magnitude representation.

(16) RT_IMU_scaler.txt: The RT_IMU_scaler module handles incoming IMU data. It receives textual input coming in from the IMU board, parses and formats it into workable objects. Then, it scales each of the samples according to the previously measured range and biases the samples by a previously measured offset. The class IMUQuaternionsGenerator uses the scaled data to estimate quaternions from nine acceleration, gyroscope and magnetometer data points. This module continuously updates its estimation with every new incoming sample. When requested by the main entry point of the system, it outputs most current estimation. This module also computes an Euler angles representation of the orientation estimation. This format is used to conveniently display the forearm orientation to the user.

(17) SVM_classifier.txt: The SVM_classifier module implements hand-to-mouth classification using an SVM classification algorithm. The module trains a classifier based on an input dataset and a set of algorithm parameters. Then it uses the trained classifier to classify new data points, optionally in real-time. The module also exports functions which allow searching the space of parameters and kernels used by the algorithm. Supported kernels are linear and radial base functions. Supported parameters are slack penalization (C) and RBF betta parameter. By searching the space of parameters, the module facilitates selecting the optimal classifier for the problem, based on a cross validation criterion.

This invention is not limited to the software set forth in these seventeen computer program files. Other software may be employed. Depending on the particular implementation, the software used in this invention may vary.

Computers

In exemplary implementations of this invention, one or more electronic computers (e.g., servers, network hosts, client computers, integrated circuits, microcontroller, controllers, field-programmable-gate arrays, personal computers, or other onboard or remote computers) are programmed and specially adapted: (1) to control the operation of, or interface with, hardware components of a sensor system (such as a sensor system for detecting hand-to-mouth behavior), including any accelerometer, gyroscope, magnetometer or EBI sensor, including any signal generator or signal processing unit of an EBI sensor; (2) to process IMU sensor data to extract quaternions; to represent EBI sensor data by a Cole-Cole model and to determine parameters of a Cole-Cole model; (3) to perform one or more classification algorithms and to adjust parameters of classification algorithms; (4) to process sensor data (e.g., IMU or EBI sensor data) to detect hand-to-mouth behavior; (5) to perform machine learning; (6) to perform any other calculation, computation, program, algorithm, or computer function described or implied above; (7) to receive signals indicative of human input; (8) to output signals for controlling transducers for outputting information in human perceivable format; and (9) to process data, to perform computations, to execute any algorithm or software, and to control the read or write of data to and from memory devices (items 1-9 of this sentence referred to herein as the "Computer Tasks"). The one or more computers (e.g., 110, 120, 150, 151) may be in any position or positions within or outside of the sensor system. For example, in some cases (a) at least one computer is housed in or together with other components of the sensor system, such as the EBI sensor, and (b) at least one computer is remote from other components of the system. The one or more computers may communicate with each other or with other components of the system either: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, computer functions and computer tasks described or implied above. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium comprises a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, or computer function described or implied above. For example, in some cases, instructions encoded in a tangible, non-transitory, computer-accessible medium comprise instructions for a computer to perform the Computer Tasks.

Network Communication

In illustrative implementations of this invention, an electronic device (e.g., 106, 110, 112, 114, 115, 120, 121, 122, 123, 124, 125, 126, 127, 150, 151, 152) is configured for wireless or wired communication with other electronic devices in a network.

For example, in some cases, a computer (e.g., 110, 120, 150, 151) or sensor (e.g., 112, 114, 115) may each include a wireless communication module for wireless communication with other electronic devices in a network. Each wireless communication module (e.g., 130) may include (a) one or more antennas, (b) one or more wireless transceivers, transmitters or receivers, and (c) signal processing circuitry. Each wireless communication module may receive and transmit data in accordance with one or more wireless standards.

In some cases, one or more of the following hardware components are used for network communication: a computer bus, a computer port, network connection, network interface device, host adapter, wireless module, wireless card, signal processor, modem, router, computer port, cables or wiring.

In some cases, one or more computers (e.g., 110, 120, 150, 151) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), wireless standard (including IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTS (long term evolution)), or other IEEE communication standard.

Definitions

The terms "a" and "an", when modifying a noun, do not imply that only one of the noun exists.

As used herein, all anatomical terms of direction (e.g., anterior and posterior) refer to the direction that would occur if the human body were in the standard anatomical position, regardless of the actual, current position of the body. For example: (a) in the standard anatomical position, an arm is rotated such that the palm is facing forward and the thumb is pointed outwards; and (b) which portion of a forearm is the anterior region of the forearm does not change even if the forearm actually rotates such that the palm changes from facing forward to facing backwards.

To compute "based on" specified data means to perform a computation that takes the specified data as an input.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

To say that four electrodes are "crossed" or "in a crossed arrangement" means that (a) the four electrodes comprise two IC electrodes and two PU electrodes; (b) one of the IC electrodes and one of the PU electrodes are attached the posterior side of a forearm; and (c) the other IC electrode and other PU electrode are attached to the anterior side of the forearm.

"Defined Term" means a term or phrase that is set forth in quotation marks in this Definitions section.

To "detect" a phenomenon does not require direct observation of the phenomenon. For example, a phenomenon may be "detected" by inference or extrapolation. Also, for example, a phenomenon may be "detected" by performing an algorithm (such as a classification algorithm) based on other data.

For an event to occur "during" a time period, it is not necessary that the event occur throughout the entire time period. For example, an event that occurs during only a portion of a given time period occurs "during" the given time period.

"EBI" means electrical bio-impedance.

The term "e.g." means for example.

Each equation above is referred to herein by the equation number set forth to the right of the equation. For example: "Equation 1" means the equation above that has "Eq. 1" to the right of it.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

"For instance" means for example.

As used herein, a "frequency sweep" means a change in frequency over time. Non-limiting examples of a "frequency sweep" include varying frequency over a range (i) by increasing continuously or in discrete steps from the lowest to the highest frequency in the range, or (ii) by decreasing continuously or in discrete steps from the highest to the lowest frequency in the range.

To say a "given" X is simply a way of identifying the X, such that the X may be referred to later with specificity. To say a "given" X does not create any implication regarding X. For example, to say a "given" X does not create any implication that X is a gift, assumption, or known fact.

"Hand-to-mouth behavior" means behavior in which at least one finger of a subject (i) is at least partially inserted into the mouth of the subject or (ii) touches one or more teeth of the subject.

"Herein" means in this document, including text, specification, claims, abstract, and drawings.

"IC electrode" means an electrode that is part of an electrical circuit that drives an alternating electrical current through tissue.

As used herein: (1) "implementation" means an implementation of this invention; (2) "embodiment" means an embodiment of this invention; (3) "case" means an implementation of this invention; and (4) "use scenario" means a use scenario of this invention.

As used herein, an "inertial measurement unit" or "IMU" means a sensor that includes an accelerometer, gyroscope and magnetometer.

To say that a calculation is "in accordance with" a first equation means that the calculation involves (a) solving the first equation or computing a value of a side of the first equation; or (b) solving a second equation or computing a value of a side of the second equation, where the second equation is derived from the first equation, such as by algebraic manipulation of the first equation or by performing the same mathematical operation on both sides of the first equation. Non-limiting examples of "solving" an equation include solving the equation in closed form or by numerical approximation.

The term "include" (and grammatical variations thereof) shall be construed as if followed by "without limitation".

The term "or" is inclusive, not exclusive. For example, A or B is true if A is true, or B is true, or both A or B are true. Also, for example, a calculation of A or B means a calculation of A, or a calculation of B, or a calculation of A and B.

A parenthesis that surrounds words that are spelled with letters is simply to make text easier to read, by indicating a grouping of words. A parenthesis does not mean that the parenthetical material is optional or may be ignored. An Arabic numeral that is surrounded by a pair of parentheses and is directly adjacent to one of the parentheses in the pair—such as in the phrase "configuration (6,5)"—is not a reference number for a patent drawing.

As used herein, a "PD index" means an index of position along a single spatial dimension that is parallel to a proximal-distal axis of a forearm, such that: (i) there are ten indexed positions in this single dimension; (ii) the ten indexed positions are equally spaced apart from each other in this single dimension; (iii) position one is the most proximal of the positions, is distal relative to the tip of olecranon, and is located (in this single dimension) at a distance of 2.5 cm from the tip of the olecranon; (iv) position ten is the most distal of the positions, and is at the same position (in this single dimension) as the most distal tip of the radius bone of the forearm, and (v) the higher the position number, the more distal the position. For example, in the PD index, position six is more distal than position five. The PD index does not indicate position in any other spatial dimension, such as position along an axis that is perpendicular to a proximal-distal axis of a forearm.

A "(6,5) pattern" means a spatial configuration of two IC electrodes and two PU electrodes, such that one of the IC electrodes and one of the PU electrodes are at position six and the other IC electrode and other PU electrode are at position five. For purposes of the preceding sentence, the positions are indexed positions in a PD index.

A "(10,1) pattern" means a spatial configuration of two IC electrodes and two PU electrodes, such that one of the IC electrodes and one of the PU electrodes are at position ten and the other IC electrode and other PU electrode are at position one. For purposes of the preceding sentence, the positions are indexed positions in a PD index.

A pair of "PU electrodes" means a first electrode and a second electrode that are electrically connected to a sensor for measuring a voltage difference between voltage at the first electrode and voltage at the second electrode, which voltage difference is due at least in part to impedance in tissue. A "PU electrode" is an electrode in a pair of PU electrodes.

As used herein, the term "set" does not include a group with no elements. Mentioning a first set and a second set does not, in and of itself, create any implication regarding whether or not the first and second sets overlap (that is, intersect).

"Some" means one or more.

"Subject" means a human.

As used herein, a "subset" of a set consists of less than all of the elements of the set.

To say that two IC electrodes and two PU electrodes are in "substantially a (6,5) pattern" means that (i) one of the IC electrodes and one of the PU electrodes are at position six, plus or minus a tolerance, and the other IC electrode and other PU electrode are at position 5, plus or minus the tolerance. For purposes of the preceding sentence: (a) the positions are indexed positions in a PD index for a forearm; and (b) the tolerance is a displacement, along the single dimension of the PD index, which displacement is equal to half of the distance between two adjacent positions in the PD index.

To say that two IC electrodes and two PU electrodes are in "substantially a (10,1) pattern" means that (i) one of the IC electrodes and one of the PU electrodes are at position ten, plus or minus a tolerance, and the other IC electrode and other PU electrode are at position one, plus or minus the tolerance. For purposes of the preceding sentence: (a) the positions are indexed positions in a PD index for a forearm; and (b) the tolerance is a displacement, along the single dimension of the PD index, which displacement is equal to half of the distance between two adjacent positions in the PD index.

The term "such as" means for example.

To say that a machine-readable medium is "transitory" means that the medium is a transitory signal, such as an electromagnetic wave.

A "transverse plane" of a forearm means a geometric plane that intersects the forearm and is perpendicular to a proximal-distal axis of the forearm.

A matrix may be indicated by a bold capital letter (e.g., D). A vector may be indicated by a bold lower case letter (e.g., a). However, the absence of these indicators does not indicate that something is not a matrix or not a vector.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) any two steps occur the same number of times or a different number of times during the method; (4) any combination of steps in the method is done in parallel or serially; (5) any step in the method is performed iteratively; (6) a given step in the method is applied to the same thing each time that the given step occurs or is applied to different things each time that the given step occurs; or (7) the method includes other steps, in addition to the steps described.

This Definitions section shall, in all cases, control over and override any other definition of the Defined Terms. The Applicant or Applicants are acting as his, her, its or their own lexicographer with respect to the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses.

VARIATIONS

This invention may be implemented in many different ways. Here are some non-limiting examples:

In some implementations, the sensor system (i) takes EBI, accelerometer, magnetometer, and gyroscope measurements and (ii) detects hand-to-mouth behavior based on these measurements. In other implementations, the sensor system (i) takes only EBI measurements, (ii) does not take accelerometer, magnetometer or gyroscope measurements, and (iii) detects hand-to-mouth behavior based on the EBI measurements. In other implementations, the sensor (i) takes EBI measurements, (ii) takes additional sensor measurements by a combination of one or more of an accelerometer, magnetometer or gyroscope, and (iii) detects hand-to-mouth behavior based on the EBI measurements and the additional sensor measurements.

This invention is not limited to the VCCS (voltage controlled current source) of the prototype, which is described above. Alternatively, the VCCS may comprise a combination of one or more of the following: OTAs (operational transconductance amplifiers), operational amplifiers, difference amplifiers, current mirrors, current amplifiers and resistors.

In some implementations, this invention is a method comprising, in combination: (a) an electrical bio-impedance (EBI) spectrometer taking a first set of measurements, which EBI spectrometer includes four crossed electrodes that are electrically connected to skin of a forearm of a subject, which four crossed electrodes comprise a first IC electrode, a second IC electrode, a first PU electrode and a second PU electrode, the first set of measurements being taken by (i) driving an alternating electrical current such that the alternating current (A) undergoes frequency sweeps, and (B) passes through an electrical circuit that includes the forearm and the first and second IC electrodes, and (ii) measuring, during the frequency sweeps, voltage difference between the first and second PU electrodes; (b) a magnetometer worn on the forearm taking a second set of measurements of orientation of the forearm; (c) a gyroscope worn on the forearm taking a third set of measurements of orientation of the forearm; (d) an accelerometer worn on the forearm taking a fourth set of measurements of acceleration of the forearm; and (e) one or more computers detecting, based on the first, second, third and fourth sets of measurements, hand-to-mouth behavior of the subject. In some cases, the four crossed electrodes are positioned on the forearm in substantially a (6,5) pattern. In some cases: (a) the four crossed electrodes are positioned on the forearm in substantially a (6,5) pattern; and (b) the one or more computers perform a Random Forests classification algorithm to detect the hand-to-mouth behavior. In some cases, the four crossed electrodes are positioned on the forearm in substantially a (10,1) pattern. In some cases: (a) the four crossed electrodes are positioned on the forearm in substantially a (10,1) pattern; and (b) the one or more computers perform a K-Nearest Neighbor classification algorithm to detect the hand-to-mouth behavior. In some cases, the one or more computers perform a Random Forests classification algorithm in order to detect the hand-to-mouth behavior. In some cases, during a training step, the one or more computers: (a) optimize parameters of a set of classification algorithms; and (b) select the classification algorithm, out of the set of classification algorithms, that produces the highest mean accuracy of detection of hand-to-mouth behavior. In some cases: (a) the one or more computers perform a classification algorithm to detect the hand-to-mouth behavior of the subject; and (b) training of the classification algorithm is performed on one or more persons other than the subject and is not performed on the subject. Each of the cases described above in this paragraph is an example of the method described in the first sentence of this paragraph, and is also an example of an embodiment of this invention that may be combined with other embodiments of this invention.

In some implementations, this invention is a method comprising, in combination: (a) an electrical bio-impedance (EBI) spectrometer taking EBI measurements, which EBI spectrometer includes four electrodes that are electrically connected to skin of a forearm of a subject, which four electrodes comprise a first IC electrode, a second IC electrode, a first PU electrode and a second PU electrode, the EBI measurements being taken by (i) driving an alternating electrical current such that the alternating current (A) undergoes frequency sweeps, and (B) passes through an electrical circuit that includes the forearm and the first and second IC electrodes, and (ii) measuring, during the frequency sweeps, voltage difference between the first and second PU electrodes; and (b) one or more computers detecting, based on the EBI measurements, hand-to-mouth behavior of the subject. In some cases, the four electrodes are crossed. In some cases, the four electrodes are positioned on the forearm in substantially a (6,5) pattern. In some cases: (a) the four electrodes are positioned on the forearm in substantially a (6,5) pattern; and (b) the one or more computers perform a Random Forests classification algorithm to detect the hand-to-mouth behavior. In some cases, the four electrodes are positioned on the forearm in substantially a (10,1) pattern. In some cases: (a) the four electrodes are positioned on the forearm in substantially a (10,1) pattern; and (b) the one or more computers perform a K-Nearest Neighbor classification algorithm to detect the hand-to-mouth behavior. In some cases, (a) the one or more computers perform a classification algorithm to detect the hand-to-mouth behavior of the subject; and (b) training of the classification algorithm is performed on one or more persons other than the subject and is not performed on the subject. In some cases, the method further comprises: (a) an accelerometer, magnetometer or gyroscope taking additional measurements; and (b) the one or more computers taking the additional measurements as in input, when detecting hand-to-mouth behavior of the subject. Each of the cases described above in this paragraph is an example of the method described in the first sentence of this paragraph, and is also an example of an embodiment of this invention that may be combined with other embodiments of this invention.

In some implementations, this invention is a system comprising: (a) an electrical bio-impedance (EBI) spectrometer for taking EBI measurements through four electrodes that are electrically attached to a forearm of a subject; and (b) one or more computers that are programmed to detect, based on the EBI measurements, hand-to-mouth behavior of the subject. In some cases, the one or more computers are programmed to perform a Random Forests classification algorithm in order to detect the hand-to-mouth behavior. In some cases, the one or more computers are programmed: (a) to optimize parameters of a set of classification algorithms; and (b) to select the classification algorithm, out of the set of classification algorithms, that produces the highest mean accuracy of detection of hand-to-mouth behavior. In some cases: (a) the system further comprises an accelerometer, magnetometer or gyroscope for taking additional measurements; and (b) the one or more computers are programmed to take the second set of measurements as in input, when detecting hand-to-mouth behavior of the subject. Each of the cases described above in this paragraph is an example of the system described in the first sentence of this paragraph, and is also an example of an embodiment of this invention that may be combined with other embodiments of this invention.

The above description (including without limitation any attached drawings and figures) describes illustrative implementations of the invention. However, the invention may be implemented in other ways. The methods and apparatus which are described above are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the above-mentioned implementations, embodiments and features.

What is claimed is:

1. A method comprising, in combination:
   (a) an electrical bio-impedance (EBI) spectrometer taking a first set of measurements, which EBI spectrometer includes four crossed electrodes that are electrically connected to skin of a forearm of a subject, which four crossed electrodes comprise a first IC electrode, a second IC electrode, a first PU electrode and a second PU electrode, the first set of measurements being taken by
      (i) driving an alternating electrical current such that the alternating current
         (A) undergoes frequency sweeps, and
         (B) passes through an electrical circuit that includes the forearm and the first and second IC electrodes, and
      (ii) measuring, during the frequency sweeps, voltage difference between the first and second PU electrodes;
   (b) a magnetometer worn on the forearm taking a second set of measurements of orientation of the forearm;
   (c) a gyroscope worn on the forearm taking a third set of measurements of orientation of the forearm;
   (d) an accelerometer worn on the forearm taking a fourth set of measurements of acceleration of the forearm; and
   (e) one or more computers detecting, based on the first, second, third and fourth sets of measurements, hand-to-mouth behavior of the subject.

2. The method of claim 1, wherein the four crossed electrodes are positioned on the forearm in substantially a (6,5) pattern.

3. The method of claim 1, wherein:
   (a) the four crossed electrodes are positioned on the forearm in substantially a (6,5) pattern; and
   (b) the one or more computers perform a Random Forests classification algorithm to detect the hand-to-mouth behavior.

4. The method of claim 1, wherein the four crossed electrodes are positioned on the forearm in substantially a (10,1) pattern.

5. The method of claim 1, wherein:
   (a) the four crossed electrodes are positioned on the forearm in substantially a (10,1) pattern; and
   (b) the one or more computers perform a K-Nearest Neighbor classification algorithm to detect the hand-to-mouth behavior.

6. The method of claim 1, wherein the one or more computers perform a Random Forests classification algorithm in order to detect the hand-to-mouth behavior.

7. The method of claim 1, wherein, during a training step, the one or more computers:
   (a) optimize parameters of a set of classification algorithms; and
   (b) select the classification algorithm, out of the set of classification algorithms, that produces the highest mean accuracy of detection of hand-to-mouth behavior.

8. The method of claim 1, wherein:
   (a) the one or more computers perform a classification algorithm to detect the hand-to-mouth behavior of the subject; and
   (b) training of the classification algorithm is performed on one or more persons other than the subject and is not performed on the subject.

9. A method comprising, in combination:
   (a) an electrical bio-impedance (EBI) spectrometer taking EBI measurements, which EBI spectrometer includes four electrodes that are electrically connected to skin of a forearm of a subject, which four electrodes comprise a first IC electrode, a second IC electrode, a first PU electrode and a second PU electrode, the EBI measurements being taken by
      (i) driving an alternating electrical current such that the alternating current
         (A) undergoes frequency sweeps, and
         (B) passes through an electrical circuit that includes the forearm and the first and second IC electrodes, and
      (ii) measuring, during the frequency sweeps, voltage difference between the first and second PU electrodes; and
   (b) one or more computers detecting, based on the EBI measurements, hand-to-mouth behavior of the subject.

10. The method of claim 9, wherein the four electrodes are crossed.

11. The method of claim 9, wherein the four electrodes are positioned on the forearm in substantially a (6,5) pattern.

12. The method of claim 9, wherein:
   (a) the four electrodes are positioned on the forearm in substantially a (6,5) pattern; and
   (b) the one or more computers perform a Random Forests classification algorithm to detect the hand-to-mouth behavior.

13. The method of claim 9, wherein the four electrodes are positioned on the forearm in substantially a (10,1) pattern.

14. The method of claim 9, wherein:
   (a) the four electrodes are positioned on the forearm in substantially a (10,1) pattern; and
   (b) the one or more computers perform a K-Nearest Neighbor classification algorithm to detect the hand-to-mouth behavior.

15. The method of claim 9, wherein:
   (a) the one or more computers perform a classification algorithm to detect the hand-to-mouth behavior of the subject; and (b) training of the classification algorithm is performed on one or more persons other than the subject and is not performed on the subject.

16. The method of claim 9, wherein the method further comprises:
   (a) an accelerometer, magnetometer or gyroscope taking additional measurements; and
   (b) the one or more computers taking the additional measurements as in input, when detecting hand-to-mouth behavior of the subject.

17. A system comprising:
(a) an electrical bio-impedance (EBI) spectrometer for taking EBI measurements through four electrodes that are electrically attached to a forearm of a subject; and
(b) one or more computers that are programmed
   (i) to detect, based on the EBI measurements, hand-to-mouth behavior of the subject, and
   (ii) to perform a Random Forests classification algorithm in order to detect the hand-to-mouth behavior.

18. A system comprising:
(a) an electrical bio-impedance (EBI) spectrometer for taking EBI measurements through four electrodes that are electrically attached to a forearm of a subject, and
(b) one or more computers that are programmed
   (i) to detect, based on the EBI measurements, hand-to-mouth behavior of the subject,
   (ii) to optimize parameters of a set of classification algorithms, and
   (iii) to select the classification algorithm, out of the set of classification algorithms, that produces the highest mean accuracy of detection of hand-to-mouth behavior.

* * * * *